United States Patent
Blumberg et al.

(10) Patent No.: US 9,689,044 B2
(45) Date of Patent: Jun. 27, 2017

(54) ASSAYS AND METHODS TO SEQUENCE MICROBES DIRECTLY FROM IMMUNE COMPLEXES

(75) Inventors: Richard S. Blumberg, Waltham, MA (US); Arthur Kaser, Cambrideshire (GB)

(73) Assignee: The Brigham and Women's Hospital, Inc., Boston, MA (US)

( * ) Notice: Subject to any disclaimer, the term of this patent is extended or adjusted under 35 U.S.C. 154(b) by 279 days.

(21) Appl. No.: 13/981,388

(22) PCT Filed: Jan. 26, 2012

(86) PCT No.: PCT/US2012/022727
§ 371 (c)(1),
(2), (4) Date: Aug. 13, 2013

(87) PCT Pub. No.: WO2012/103337
PCT Pub. Date: Aug. 2, 2012

(65) Prior Publication Data
US 2013/0330715 A1 Dec. 12, 2013

Related U.S. Application Data

(60) Provisional application No. 61/436,345, filed on Jan. 26, 2011.

(51) Int. Cl.
| | | |
|---|---|---|
| C12P 19/34 | (2006.01) | |
| C12Q 1/68 | (2006.01) | |
| C12Q 1/04 | (2006.01) | |
| G01N 33/68 | (2006.01) | |

(52) U.S. Cl.
CPC .............. *C12Q 1/6888* (2013.01); *C12Q 1/04* (2013.01); *C12Q 1/6806* (2013.01); *C12Q 1/689* (2013.01); *C12Q 1/6883* (2013.01); *G01N 33/68* (2013.01); *G01N 2800/26* (2013.01)

(58) Field of Classification Search
None
See application file for complete search history.

(56) References Cited

U.S. PATENT DOCUMENTS

| | | | |
|---|---|---|---|
| 2004/0005592 A1* | 1/2004 | Emtage | C07K 14/47 |
| | | | 435/6.16 |
| 2009/0111102 A1 | 4/2009 | Diehl et al. | |
| 2010/0151445 A1 | 6/2010 | Charpentier et al. | |

OTHER PUBLICATIONS

Clarridge (2004) Clinical. Microbiol. Rev. vol. 17 No. 4. pp. 840-862.*
Nakamura et al. (2009) pLos One vol. 4 (1): e4219. doi:10.1371/journal.pone.0004219.*
Segal et al. (1997) J Immunol. 158: 5087-5090.*
Vaneechoutte et al. (1997) J. med. Microbiol vol. 46: 188-194.*
Zhou et al. "Analysis of Hepatitis B Virus-Immunoglobulin isotype complexes by a novel immuno-capture polymerase chain reaction method." Scandinavian Journal of Immunology, 57:391-396 (2003).
Macpherson et al. "Mucosal antibodies in inflammatory bowel disease are directed against intestinal bacteria." Gut, 38:365-375 (1996).
De Palma et al. "Intestinal dysbiosis and reduced immunoglobulin-coated bacteria associated with coeliac disease in children." BMC Microbiology, 10:63 (2010).
Nilsson et al. "Fractionation of rat IgG subclasses and screening for IgG Fc-binding to bacteria." Molecular Immunology, 19(1):119-126 (1982).
Frank et al., PNAS USA, 104(34):13780-13785 (2007). "Molecular-phylogenetic characterization of microbial community imbalances in human inflammatory bowel diseases."
Peterson et al., Cell Host Microbe, 3(6):417-427 (2008). "Metagenomic approaches for defining the pathogenesis of inflammatory bowel diseases."
Urbach et al., Appl Environ Microbiol, 65(3):1207-1213 (1999). "Immunochemical detection and isolation of DNA from metabolically active bacteria."

* cited by examiner

*Primary Examiner* — Kenneth Horlick
(74) *Attorney, Agent, or Firm* — Nixon Peabody LLP; Mark J. FitzGerald; Srividya Subramanian

(57) ABSTRACT

Provided herein are MiIP-Seq assays and methods for detecting and/or identifying an immune-stimulating microbe in a patient sample. Also provided herein are methods for diagnosing an infectious disease or identifying a previously uncharacterized microbe in a patient sample. The methods and assays described herein are advantageous over existing methods in that they (i) do not require a culture step for microbe expansion, (ii) are not specific for a particular microbe and can be used to identify a previously uncharacterized microbe, and (iii) permits rapid processing due to the lack of a microbe culture step.

19 Claims, 12 Drawing Sheets

ASSAYS AND METHODS TO SEQUENCE MICROBES DIRECTLY FROM IMMUNE COMPLEXES

CROSS-REFERENCE TO RELATED APPLICATIONS

This application is a 35 U.S.C. §371 National Phase Entry Application of International Application No. PCT/US2012/022727 filed Jan. 26, 2012, which designates the U.S., and which claims benefit under 35 U.S.C. §119(e) of U.S. Provisional Patent Application No. 61/436,345 filed on Jan. 26, 2011, the contents of which are incorporated herein by reference in their entireties.

GOVERNMENT SUPPORT

This invention was made with Government support under Grant Nos. DK044319 awarded by the National Institutes of Health (NIH). The Government has certain rights in this invention.

FIELD OF THE INVENTION

The field of the invention relates to the detection and identification of immune system-stimulating microbes and the diagnosis of infectious disease.

BACKGROUND

An estimated 1 million Americans suffer from chronic inflammatory bowel disease (IBD). IBD, such as Crohn's Disease (CD) and ulcerative colitis (UC). These diseases are characterized by a chronic inflammatory response that results in histologic damage to the intestinal lining Both CD and UC exhibit large numbers of leukocytes that migrate to the mucosa and into the intestinal lumen. Both diseases oscillate between active (i.e., presence of intestinal inflammation) and inactive (i.e., minimal to no intestinal inflammation) stages of disease activity. Active IBD can include symptoms such as bloody diarrhea, abdominal pain, and fever. The inactive stage has minimal to no intestinal inflammation and lacks severe gastrointestinal illness. It has been postulated that an inappropriate immune response to commensal bacteria is one cause of inflammatory bowel disease. An inappropriate immune response can result in the formation of immune complexes, e.g., a combination of an antibody molecule and an antigen. Antigens can be foreign substances, such as viral or bacterial polypeptides. Antibodies can prevent infections by coating viruses or bacteria.

SUMMARY OF THE INVENTION

The assays and methods described herein provide direct methods by which to detect and/or identify microbes to which one or more components of the innate or adaptive immune system are responding. Such methods are unique in their ability to determine which microbes are being recognized by the immune system as foreign antigens, rather than simply detecting the presence of microbes. Since many microbes can be present without causing disease (e.g., commensal bacteria), measuring the level of microbes does not necessarily indicate that a microbe is pathogenic to the subject in which it is detected. However, the methods described herein, permit the detection of microbes to which the subject's body is mounting an immune response, and are referred to herein as "Microbe Immunoprecipitation and Sequencing" or "MiIP-Seq" methods. This distinction can be especially important in, for example, diseases wherein an immune response is raised against a particular antigen in a subset of individuals, where such a reaction does not occur in most individuals in the population, for example, in individuals suffering from an autoimmune conditions. Another example include inflammatory bowel disease (IBD), which is thought to result, in some cases, from an inappropriate immune response to commensal microbiota. Accordingly, the assays and methods described herein permit, in some embodiments, the detection and/or identification of commensal microbiota (including bacteria, viruses and other microorganisms) that specifically elicit an immune response in, e.g., those with inflammatory bowel disease, and permit the diagnosis of infectious disease.

Accordingly, provided herein are assays and methods for detecting and/or identifying an immune-stimulating microbe in a patient sample. Also provided herein are methods for diagnosing an infectious disease or identifying a novel pathogen in a patient sample.

Accordingly, in some aspects, provided herein are methods for identifying or diagnosing the presence of an immune-stimulating microbe in a patient having a disease or disorder, the methods comprising: (a) extracting nucleic acids from an immune protein-enriched fraction obtained from a patient sample, (b) sequencing the extracted nucleic acids, and (c) comparing the sequence of the extracted nucleic acids to known microbial nucleic acid sequences to identify whether the nucleic acids extracted from the immune protein-enriched fraction are microbial, wherein if the extracted nucleic acids are microbial, the patient is diagnosed as having an immune-stimulating microbe. In some aspects, provided herein are methods for identifying or diagnosing the presence of an immune-stimulating microbe in a patient having a disease or disorder, the method comprising: (a) preparing an immune protein-enriched fraction from a patient sample, (b) extracting nucleic acids from the immune protein-enriched fraction, (c) sequencing the extracted nucleic acids, and (d) comparing the sequence of the extracted nucleic acids to known microbial nucleic acid sequences to identify whether the nucleic acids extracted from the immune protein-enriched fraction are microbial, wherein if the extracted nucleic acids are microbial, the patient is diagnosed as having an immune-stimulating microbe.

In some embodiments of these methods and all such methods described herein, the patient having a disease or disorder has an inflammatory bowel disease. In some such embodiments, the inflammatory bowel disease is Crohn's disease, ulcerative colitis, collagenous colitis, lymphocytic colitis, ischemic colitis, diversion colitis, Behcet's syndrome, or indeterminate colitis.

In some embodiments of these methods and all such methods described herein, the patient having a disease or disorder has an autoimmune disorder.

In some embodiments of these methods and all such methods described herein, the patient having a disease or disorder has cirrhosis, sepsis, or viremia.

In some embodiments of these methods and all such methods described herein, the immune protein-enriched fraction is prepared using an affinity binding agent specific for an immunoglobulin, a complement protein, or a pathogen recognition receptor.

In some embodiments of these methods and all such methods described herein, the immune protein-enriched fraction is prepared using an affinity binding agent specific for IgA, IgD, IgE, IgG, IgM, or any combination thereof.

In some embodiments of these methods and all such methods described herein, the immune protein-enriched fraction is prepared using an affinity binding agent specific for IgG.

In some embodiments of these methods and all such methods described herein, the immune protein-enriched fraction is prepared by immunoprecipitation using an affinity binding agent.

In some embodiments of these methods and all such methods described herein, the affinity binding agent is protein A, protein G, protein A/G, protein L, an immune protein-specific antibody or fragment thereof, or any combination thereof.

In some embodiments of these methods and all such methods described herein, an affinity binding agent or immune protein-specific antibody used in the methods comprises an anti-human IgG, an anti-human IgA, an anti-human IgD, an anti-human IgE, an anti-human IgM, or any combination thereof agent or antibody.

In some embodiments of these methods and all such methods described herein, an affinity binding agent used in the methods is specific for an immunoglobulin immune protein and binds to an epitope on the Fc fragment of the immunoglobulin immune protein.

In some embodiments of these methods and all such methods described herein, an affinity binding agent used in the methods is not bound to a solid phase support.

In some embodiments of these methods and all such methods described herein, an affinity binding agent used in the methods is bound to a solid phase support. In some such embodiments, the solid phase support comprises superparamagnetic microbeads, microscopic agarose beads, or agarose resin beads.

In some embodiments of these methods and all such methods described herein, the immune system-stimulating microbe being detected is a bacterium, fungus or a virus.

In some embodiments of these methods and all such methods described herein, the immune system-stimulating microbe being detected belongs to the taxon domain Archae, Bacteria, or Eukarya.

In some embodiments of these methods and all such methods described herein, the patient sample is a blood sample, a plasma sample, a urine sample, a cerebrospinal fluid sample, a mucous membrane sample, a fecal sample, an intestinal lavage sample, an intestinal fluid sample, a joint fluid sample, a respiratory sputum sample, or a bronchoalveolar lavage fluid sample. In some such embodiment, the intestinal lavage sample is an ileal lavage sample.

In some embodiments of these methods and all such methods described herein, the immune system-stimulating microbe being detected is a previously uncharacterized microbe.

In some embodiments of these methods and all such methods described herein, the sequencing step is performed using shotgun cloning, 16S rRNA/DNA amplification, and/or metagenomic sequencing.

In some embodiments of these methods and all such methods described herein, the sequencing of step (b) or step (c) is performed using microbe gene-specific primers.

In some embodiments of these methods and all such methods described herein, the sequencing of step (b) or step (c) is performed using primers that are not gene-specific.

In some embodiments of these methods and all such methods described herein, the patient sample from which the immune protein-enriched fraction is prepared does not undergo a cultivation step prior to the step of extracting nucleic acids.

Also provided herein, in some aspects are assays for direct detection of an immune system-stimulating microbe in a patient sample, the assays comprising the steps of: (a) extracting nucleic acids from the immune protein-enriched fraction prepared from a patient sample, and (b) sequencing the extracted nucleic acids present in the immune protein-enriched fraction to obtain a sequence of any immune system-stimulating microbes present in the patient sample.

In some aspects, also provided herein are assays for direct detection of an immune system-stimulating microbe in a patient sample, the assays comprising the steps of: (a) preparing an immune protein-enriched fraction from a patient sample, (b) extracting nucleic acids from the immune protein-enriched fraction, and (c) sequencing the extracted nucleic acids present in the immune protein-enriched fraction to obtain a sequence of any immune system-stimulating microbes present in the patient sample.

In some embodiments of these assays and all such assays described herein, the immune protein-enriched fraction is prepared using an affinity binding agent specific for an immunoglobulin, a complement protein, or a pathogen recognition receptor.

In some embodiments of these assays and all such assays described herein, the immune protein-enriched fraction is prepared using an affinity binding agent specific for IgA, IgD, IgE, IgG, IgM, or any combination thereof.

In some embodiments of these assays and all such assays described herein, the immune protein-enriched fraction is prepared using an affinity binding agent specific for IgG.

In some embodiments of these assays and all such assays described herein, the immune protein-enriched fraction is prepared by immunoprecipitation using an affinity binding agent. In some such embodiments, the affinity binding agent is protein A, protein G, protein A/G, protein L, an immune protein-specific antibody or fragment thereof, or any combination thereof.

In some embodiments of these assays and all such assays described herein, an affinity binding agent or immune protein-specific antibody used comprises anti-human IgG.

In some embodiments of these assays and all such assays described herein, an affinity binding agent used is specific for an immunoglobulin immune protein and binds to an epitope on the Fc fragment of the immunoglobulin immune protein.

In some embodiments of these assays and all such assays described herein, an affinity binding agent used is not bound to a solid phase support. In some embodiments of these assays and all such assays described herein, an affinity binding agent used is bound to a solid phase support. In some such embodiments, the solid phase support comprises superparamagnetic microbeads, microscopic agarose beads, or agarose resin beads.

In some embodiments of these assays and all such assays described herein, the immune system-stimulating microbe being detected is a bacterium, fungus or a virus.

In some embodiments of these assays and all such assays described herein, the immune system-stimulating microbe being detected belongs to the taxon domain Archae, Bacteria, or Eukarya.

In some embodiments of these assays and all such assays described herein, the patient sample is a blood sample, a plasma sample, a urine sample, a cerebrospinal fluid sample, a mucous membrane sample, a fecal sample, an intestinal lavage sample, an intestinal fluid sample, a joint fluid sample, a respiratory sputum sample, or a bronchoalveolar lavage fluid sample. In some such embodiments, the intestinal lavage sample is an ileal lavage sample.

In some embodiments of these assays and all such assays described herein, the immune system-stimulating microbe being detected is a previously uncharacterized microbe.

In some embodiments of these assays and all such assays described herein, the sequencing step is performed using shotgun cloning, 16S rRNA/DNA amplification, and/or metagenomic sequencing.

In some embodiments of these assays and all such assays described herein, the sequencing of step (b) or step (c) is performed using microbe gene-specific primers.

In some embodiments of these assays and all such assays described herein, the sequencing of step (b) or step (c) is performed using primers that are not gene-specific.

In some embodiments of these assays and all such assays described herein, the patient sample from which the immune protein-enriched fraction is prepared does not undergo a cultivation step prior to the step of extracting nucleic acids.

In some embodiments of these assays and all such assays described herein, the microbe cannot be cultivated using standard cultivation conditions.

Also provided herein, in some aspects, are systems for obtaining data from at least one test sample comprising nucleic acids extracted from an immune-protein enriched sample obtained from an at least one patient, the systems comprising: a determination module configured to receive said at least one test sample comprising the extracted nucleic acids and perform at least one sequencing analysis on said at least one test sample to generate a sequencing data output; a storage device configured to store said sequencing data output from said determination module; a comparison module configured to receive said sequencing data output of the test sample comprising extracted nucleic acids and perform at least one sequencing analysis on said sequencing data output to determine the presence or absence of one of the following conditions and produce a comparison data output: (i) the extracted nucleic acid sequence has 20% homology or greater to a sequence of a known family of microbes; or (ii) the extracted nucleic acid sequence has less than 20% homology to a sequence of a known family of microbes; and a display module for displaying a content based in part on the comparison data output from said comparison module, wherein the content comprises a signal indicative that the extracted nucleic acid sequence has 20% homology or greater to a sequence of a known family of microbes; or signal indicative that the extracted nucleic acid sequence has less than 20% homology to a sequence of a known family of microbes.

In some embodiments of these systems and all such systems described herein, the content displayed on said display module further comprises a signal indicative of the patient being recommended to receive a particular treatment regimen.

DEFINITIONS

For convenience, certain terms employed herein, in the specification, examples and appended claims are collected here. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

As used herein, the term "inflammatory bowel disease" ("IBD") includes inflammatory bowel disease of any type, etiology or pathogenesis. It includes, without limitation, ulcerative colitis, collagenous colitis, colitispolyposa, transmural colitis, segmental colitis, Crohn's disease, indeterminate colitis, lymphocytic colitis, ischemic colitis, diversion colitis, Behcet's syndrome, infectious colitis, and the like.

As used herein, the term "autoimmune disease" refers to a condition that is immune-mediated due to an attack on self-tissues, such as when a subject's own antibodies react with host tissue or in which immune effector T cells are autoreactive to endogenous self-peptides and cause destruction of tissue, but can also involve an immune response to a microorganism. Such conditions include, but are not limited to, autoimmune diabetes mellitus (type 1 diabetes mellitus; insulin-dependent diabetes mellitus), ANCA-positive vasculitis, rheumatoid arthritis, systemic lupus erythematosus (SLE), Sjogren's disease or syndrome, dermatomyositis, psoriasis, primary sclerosing cholangitis, primary biliary cirrhosis, autoimmune hepatitis, multiple sclerosis, ankylosing spondylitis, autoimmune encephalomyelitis, myasthenia gravis (MG), autoimmune lymphoproliferative syndrome (ALPS), Hashimoto's thyroiditis, Goodpasture's syndrome, pemphigus (e.g., pemphigus vulgaris), Grave's disease, autoimmune hemolytic anemia, autoimmune hemophilia, autoimmune thrombocytopenic purpura, scleroderma with anti-collagen antibodies, mixed connective tissue disease, polymyositis, pernicious anemia, idiopathic Addison's disease, autoimmune-associated infertility, glomerulonephritis (e.g., crescentic glomerulonephritis, proliferative glomerulonephritis), bullous pemphigoid, autoimmune uveoretinitis, glomerulonephritis, and Guillain-Barre syndrome. In one embodiment, the autoimmune disease is selected from the group consisting of multiple sclerosis, type-I diabetes, Hashinoto's thyroiditis, rheumatoid arthritis, systemic lupus erythematosus, autoimmune hepatitis, hemolytic anemia, autoimmune hemophilia, autoimmune lymphoproliferative syndrome (ALPS), autoimmune uveoretinitis, glomerulonephritis, Guillain-Barre syndrome, psoriasis and myasthenia gravis.

As used herein, the term "direct detection" refers to the ability of the methods described herein to assay for the presence and identity of a microbe directly from the immune protein-enriched fraction (e.g., by sequencing) without the use of assays that indirectly test for a microbe (e.g., ELISA of IgG raised against the microbe). The methods described herein employ "direct detection," which has the added advantages of being able to identify a microbe that has not been previously characterized in an unbiased manner by taking advantage of the innate and/or adaptive immune response to a microbe. This is useful when e.g., the IgG antibody against the microbe is not known, the microbe is not cultivatable using standard techniques to enhance detection, and/or there is no existing ELISA test for the anti-microbe antibody.

As used herein, the term "immune system-stimulating microbe" refers to a bacterium, a fungus, or a virus that is recognized by a subject's innate or acquired immune system, thereby raising an immune-mediated response to the microbe in the subject. An immune system-stimulating microbe can be from the taxon domain Archaea, Bacteria, or Eukarya. Typically, immune system-stimulating microbes are "pathogenic," as the term is defined herein, however in some cases a typically non-pathogenic microbe (e.g., a commensal bacteria) can still raise an immune-mediated response in a subset of subjects in a population (e.g., subjects having inflammatory bowel disease). Thus, the term "immune system-stimulating microbe" is not used interchangeably with "pathogenic" herein. In one embodiment, the immune stimulating microbe is not a horse pathogen, such as *Ehrlichia risticii*.

As used herein, the terms "patient sample" or "biological sample" refers to a fluid sample, a cell sample, a tissue sample or an organ sample obtained from a patient. In some embodiments, a cell or population of cells, or a quantity of tissue or fluid are obtained from a subject. Often, a "patient sample" can comprise cells from the animal, but the term can also refer to non-cellular biological material, such as non-cellular fractions of blood, saliva, or urine, that can be used to detect the presence or identity of a microbe. Biological samples include, but are not limited to, tissue biopsies, scrapes (e.g. buccal scrapes), whole blood, plasma, serum, urine, saliva, cell culture, tissue biopsies, mucous membrane samples, feces, intestinal lavage, joint fluid, cerebrospinal fluid, a biliary sample, a respiratory secretion, such as sputum, brochoalveolar lavage fluid sample, and the like. A biological sample or tissue sample can refer to a sample of tissue or fluid isolated from an individual, including but not limited to, for example, blood, plasma, serum, urine, stool, sputum, spinal fluid, pleural fluid, lymph fluid, the external sections of the skin, respiratory, intestinal, and genitourinary tracts, tears, saliva, and organs. Samples can include frozen tissue. The term "sample" also encompasses any material derived by further processing such a sample. Derived samples can, for example, include nucleic acids or proteins extracted from the sample or obtained by subjecting the sample to techniques such as amplification of nucleic acids or reverse transcription of mRNA, isolation and/or purification of certain nucleic acids, proteins, other cytoplasmic or nuclear components, etc.

The terms "patient", "subject" and "individual" are used interchangeably herein, and refer to an animal, particularly a human, to whom it is desirable to analyze for the presence of immune system-stimulating microbes in a biological sample obtained from the subject. In some embodiments, a subject is need of diagnosis of a disease or disorder, for example, diagnosis of inflammatory bowel disease, whereby a biological sample is analyzed using the methods and assays described herein. The term "subject" or "patient" as used herein also refers to human and non-human animals. The term "non-human animals" includes all vertebrates, e.g., mammals, such as non-human primates, (particularly higher primates), sheep, dog, rodent (e.g. mouse or rat), guinea pig, goat, pig, cat, rabbits, cows, and any domestic animal or pet, as well as non-mammals such as chickens, amphibians, reptiles etc. In one embodiment, the subject is human. In some embodiments, the subject is not a horse.

As used herein, the term "immune protein-enriched fraction" refers to a sample that is partially purified (e.g., by immunoprecipitation) such that the level of a desired immune protein (e.g., immunoglobulins, complement, or other soluble/circulating components of the innate or adaptive immune response) is increased in the sample by at least 10% compared to the original patient sample from which it is derived. In some embodiments, the immune protein level is increased in the enriched fraction by at least 20%, at least 30%, at least 40%, at least 50%, at least 60%, at least 70%, at least 80%, at least 90%, at least 95%, at least 99%, at least 1-fold, at least 2-fold, at least 5-fold, at least 10-fold, at least 25-fold, at least 50-fold, at least 100-fold, at least 1000-fold, or more, compared to the patient sample from which it is derived.

As used herein, the term "immunoglobulin" refers to an antibody typically found in blood or other bodily fluids of a subject, which are used to identify and neutralize foreign antigens such as bacteria or viruses. In general, an immunoglobulin comprises two large heavy chains and two small light chains and are produced by white blood cells. There are five different antibody isotypes (i.e., IgA, IgD, IgE, IgG and IgM) known in mammals, which perform different roles, and help direct the appropriate immune response for each different type of foreign object they encounter.

The term "antibody," as used herein, refers to a protein produced by the immune system that protects the organism against an antigen, and naturally occurring variants thereof. An "antibody" typically comprises at least two heavy (H) chains and two light (L) chains inter-connected by disulfide bonds. Each heavy chain is comprised of a heavy chain variable region and a heavy chain constant region. The heavy chain constant region is comprised of three domains, CH1, CH2 and CH3. Each light chain is comprised of a light chain variable region and a light chain constant region. The light chain constant region is comprised of one domain, CL. The variable heavy and variable light regions can be further subdivided into regions of hypervariability, termed complementarity determining regions (CDR), interspersed with regions that are more conserved, termed framework regions (FR). Each variable heavy and variable light chain is composed of three CDRs and four FRs, arranged from amino-terminus to carboxyl-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

As used herein, the term "previously uncharacterized microbe" refers to a microbe that has an unknown function or a novel microbe that has not been previously identified or sequenced. Such microbes are sequenced using random primers and in accordance with embodiments of the methods described herein. The sequences are then compared to known sequences for microbes, e.g., a database of microbe sequences, such as GenBank or a metagenomic library database, to permit identification (e.g., using a search engine such as BLAST or an alignment tools such as ClustalW). A previously uncharacterized microbe is identified as such if there is little or no homology (e.g., less than 20%) to another microbe in the database. In some embodiments, the previously uncharacterized microbe will have sequence homology to a microbe in the database, however the database does not indicate that a function for the microbe is known.

As used herein, the phrase "does not undergo a cultivation step" indicates that the immune-protein fraction is not cultured using standard techniques to amplify the number of microbes in the sample prior to extraction and sequencing of the nucleic acids.

As used herein, the phrase "cannot be cultivated using standard cultivation conditions" refers to a microbe that does not grow or amplify under standard cultivation conditions (e.g., for bacteria standard culture conditions include e.g., growth in Lysogeny Broth (LB media) for at least 14 h at 37° C., shaking continuously). For example, the microbe can have an optimal growth temperature that is higher or lower than those used under standard cultivation conditions, or the microbe requires an essential nutrient that is not present in standard cultivation media, thus not permitting one to grow or propagate the microbe in standard conditions to enhance detection. Similarly, in the case of viral microbes, "cannot be cultivated using standard cultivation conditions" can refer to the lack of a host cell to propagate the virus in, for example. One of skill in the art is aware of standard growth techniques and conditions for microbes, such as bacteria and viruses, and can easily apply this knowledge to the methods and assays described herein.

As used herein, the term "known sequences for microbes" refers to, e.g., a database of microbial gene sequences, such as GenBank, and the sample sequences can be identified using search tools such as BLAST to query the database for nucleic acid sequence homology. In some embodiments, the known sequences are compared to sequences in a metagenomic library database. The term "control sample" encompasses nucleic acids of an individual or a plurality of individuals with no detectable disease that have been prepared and sequenced using the methods and assays described herein.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and the include plural references unless the context clearly dictates otherwise. Thus for example, references to "the method" includes one or more methods, and/or steps of the type described herein and/or which will become apparent to those persons skilled in the art upon reading this disclosure and so forth.

The practice of the methods described herein will employ, unless otherwise indicated, conventional techniques of molecular biology, microbiology and recombinant DNA techniques, which are within the skill of the art. Such techniques are explained fully in the literature. See, e.g., Sambrook, Fritsch & Maniatis, 1989, Molecular Cloning: A Laboratory Manual, Second Edition; Oligonucleotide Synthesis (M. J. Gait, ed., 1984); Polynucleotide Hybridization (B. D. Harnes & S. J. Higgins, eds., 1984); A Practical Guide to Molecular Cloning (B. Perbal, 1984); and a series, Methods in Enzymology (Academic Press, Inc.); Short Protocols In Molecular Biology, (Ausubel et al., ed., 1995).

It is understood that the following detailed description and examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified in the specification and examples are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

BRIEF DESCRIPTION OF THE FIGURES

FIG. 1A shows an ileal lavage sample of a first patient, while FIG. 1B shows the same ileal lavage sample immunoprecipitated using uncoated beads (i.e., control), and FIG. 1C shows an IgG-enriched fraction prepared by immunoprecipitation of the ileal lavage sample using anti-human-IgG coated beads. A difference in abundance of 10 PCR cycles was observed between the IgG enriched fraction and the control uncoated beads fraction (i.e., greater than 1000-fold enrichment in the IgG beads over the control beads). DNA was isolated from anti-IgG beads and control beads after undergoing immunoprecipitation procedures from intestinal lavages as described herein, as well as from input-lavage; primers amplifying the V2 region of 16S DNA with appropriate adapters and linkers attached were used to generate a library that was then sequenced on a 454 sequencer. FIGS. 1A-1C show the relative abundance of sequences assigned to individual operational taxonomic units OTUs based on V2 homology and using public databases, such as greengenes.lbl.gov, found on the worldwide web, in anti-IgG immunoprecipitated lavage compared to control-precipitated lavage and input-lavage. To permit a qualitative comparison, the control bead immunoprecipitated DNA was amplified more extensively than the IgG beads DNA. The bacterial community in the lavage is very similar in composition to that precipitated with the control beads but is very different from the bacterial community pulled down by the IgG beads. Thus, the bacteria in the IgG-enriched fraction are immune system-stimulating microbes, as that term is used herein.

FIG. 2A shows an ileal lavage sample of a second patient, FIG. 2B shows the ileal lavage sample immunoprecipitated using uncoated beads (i.e., control), and FIG. 2C shows an IgG-enriched fraction prepared by immunoprecipitation of the ileal lavage sample using anti-human-IgG coated beads. DNA was isolated from anti-IgG beads and control beads after undergoing immunoprecipitation procedures from intestinal lavages as described herein, as well as from input-lavage; primers amplifying the V2 region of 16S DNA with appropriate adapters and linkers attached were used to generate a library that was then sequenced on a 454 sequencer. FIGS. 1A-1C show the relative abundance of sequences assigned to individual operational taxonomic units OTUs based on V2 homology and using public databases, such as greengenes.lbl.gov, found on the worldwide web, in anti-IgG immunoprecipitated lavage compared to control-precipitated lavage and input-lavage. To permit a qualitative comparison, the control bead immunoprecipitated DNA was amplified more extensively than the IgG beads DNA. The bacterial community in the lavage is very similar in composition to that precipitated with the control beads but is very different from the bacterial community pulled down by the IgG beads. Thus, the bacteria in the IgG-enriched fraction are immune system-stimulating microbes, as that term is used herein.

DETAILED DESCRIPTION

Figure 1A:
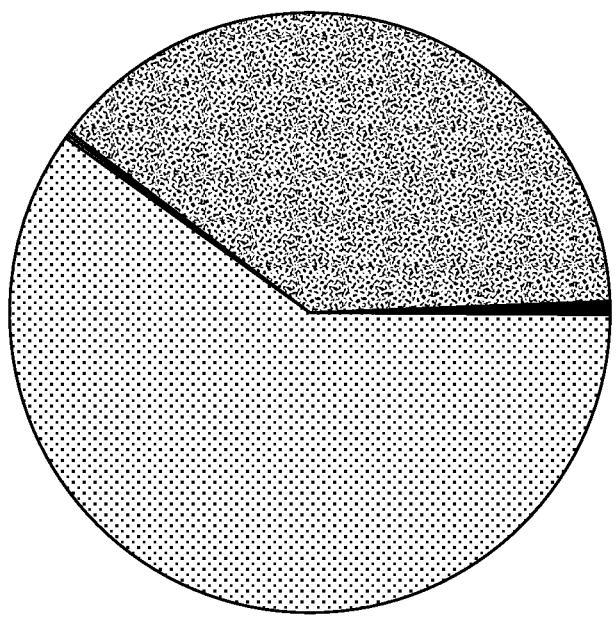
FIGS. 1A-1C depict a series of pie charts showing the proportion of bacteria in ileal lavage samples.

Provided herein are "MiIP-Seq" (Microbe ImmunoPrecipitation and Sequencing) assays and methods for detecting and/or identifying an immune-stimulating microbe in a patient sample. Also provided herein are methods for diagnosing an infectious disease or identifying a previously uncharacterized microbe in a patient sample. The methods and assays described herein are advantageous over existing methods in that they (i) do not require a culture step for microbe expansion, (ii) are not specific for a particular microbe and can be used to identify a previously uncharacterized microbe, and (iii) permit rapid processing due to the lack of a microbe culture step.

The mammalian host (human and non-human) is colonized by a wide variety of either commensal or pathogenic microbes. Whether the immune system responds to a microbe is indicative of whether the microbe is commensal or pathogenic to the host. Current microbiologic methods do not necessarily take into account the immune response to an organism as a means to directly identify the organism. The presence of a microbe is typically determined by cultivation or similar types of biologic assays. However, the mere presence of a microbe does not indicate or determine whether the microbe is causing harm to the host. For example, microbes that are commensal in some individuals can be pathogenic in other individuals.

In contrast, the assays and methods described herein take advantage of immune proteins generated during an immune response for the direct detection of microbes, in order to identify and distinguish microbes mediating specific diseases and disorders, especially those in which the organism cannot be cultivated. Moreover, the methods described herein are amenable to a broad range of direct analysis of biological samples, such as bodily fluids.

More specifically, the assays and methods described herein are directed to the detection of microbes that stimulate the immune system and elicit the production of immune proteins by one or more cells or components of the immune system. By explicitly targeting microbes bound by immune proteins in the form of immune complexes, the methods and assays described herein permit detection and/or identification of only those microbes eliciting immune responses in a biological sample from a host, as opposed to microbes that are present but not causing the host harm, such as, for example, a commensal microbe. Thus, the methods and assays described herein provide targeted and unbiased approaches for identification and enrichment of those microbes eliciting an immune response by focusing on immune proteins bound to microbes, versus microbial detection alone.

Immune Proteins and Immune Complexes

The methods and assays described herein are directed to the detection of microbes that stimulate the immune system and elicit the production of immune proteins by one or more cells or components of the immune system. Thus, the method and assays described herein involve, in some embodiments, the detection of one or more immune proteins or immune complexes.

As used herein, the phrases "immune system-stimulating microbe" or "microbe(s) that stimulate(s) the immune system," refer to a microbe, such as a bacterium, a fungus, or a virus, that is both recognized by a subject's or host's innate or acquired immune system, and elicits an immune-mediated response in the subject. An immune system-stimulating microbe can be from the taxon domain Archaea, Bacteria, or Eukarya. Typically, immune system-stimulating microbes are "pathogenic," as the term is defined herein, however in some cases a typically non-pathogenic microbe (e.g., a commensal bacteria) can still raise an immune-mediated response in a subset of subjects in a population (e.g., subjects having inflammatory bowel disease). Thus, the term "immune system-stimulating microbe" is not used interchangeably with "pathogenic" herein.

Essentially any protein activated or secreted in response to a foreign microbe or involved in immune-mediated removal or binding of a microbe can be used to prepare an immune protein-enriched fraction in conjunction with the methods and assays described herein. During an immune response, a number of proteins are secreted or produced that can bind to or immobilize a microbe. Such immune proteins when bound to a microbe, either specifically (such as, for example, antibodies) or non-specifically (such as, for example, components of the complement cascade), form "immune complexes," are used in the methods and assays described herein to facilitate the detection and/or identification of those microbes that elicit an immune response.

As used herein, an "immune complex" refers to the integral binding of an immune protein, such as an antibody or complement molecule, to a soluble antigen, such as a microbe. Such immune complexes comprising bound microbe can be identified and/or precipitated using the methods and assays described herein. In some embodiments of the aspects described herein, the immune protein is a protein of the adaptive immune system (e.g., an immunoglobulin). In other embodiments of the methods described herein, the immune protein is an immune protein of the innate immune system (e.g., a complement component).

Complement System

In some embodiments of the aspects described herein, a complement protein can be the immune protein or component of an immune protein-enriched fraction detected or targeted using the methods and assays described herein. The complement system refers to a biochemical cascade that aids antibodies (e.g., immunoglobulins) and cells of the immune system in the clearance of pathogens from an organism. It is part of the immune system traditionally called the innate immune system that is not adaptable (i.e., does not change over the course of an individual's lifetime). However, it can both recruit and bring into action components of the adaptive immune system, and can be recruited and brought into action by components of the adaptive immune system.

The complement system comprises small proteins in the blood that are stimulated by one of several triggers and which induce proteases in the system to cleave specific proteins to release cytokines and initiate an amplifying cascade of further cleavages. The end-result of this activation cascade is amplification of the response and activation of the cell-killing membrane attack complex. Over 25 proteins and protein fragments make up the complement system, including serum proteins, serosal proteins, and cell membrane receptors. The complement system is typically divided into the classical complement pathway, the alternative complement pathway, and the mannose-binding lectin pathway. Any of the proteins of the complement system that can bind to or remove a microbe, such as a bacterium, fungus, or virus, can be used to prepare an immune protein-enriched fraction for use with the methods and assays described herein.

Components of the classical complement pathway include the C1-complex (composed of 1 molecule of C1q, 2 molecules of C1r and 2 molecules of C1s, thus forming C1qr2s2), which forms when C1q binds to IgM or IgG complexed with antigens, or when C1q binds directly to the surface of the pathogen; C4 and fragments thereof (C4a and C4b); C2 and fragments thereof (C2a and C2b); the classical pathway C3 convertase, comprising C4b and C2a; C3 and fragments thereof (C3a and C3b); C5 convertase (comprising C4b, C2a, and C3b); C5 and fragments thereof (C5a and C5b); C6; C7; C8; C9; and the membrane attack complex (comprising C5b, C6, C7, C8, and C9). C3b can also bind to the surface of pathogens. Accordingly, in some embodiments of the methods and assays described herein, the immune protein is C1-complex, C1q, C3b, or the membrane attack complex comprising C5b, C6, C7, C8, and C9.

Components of the alternative complement pathway include C3 and fragments thereof (C3a and C3b), the formation of which are triggered by spontaneous C3 hydrolysis directly due to the breakdown of the thioester bond via condensation reaction; Factor B; the complex C3bB, which forms upon binding of Factor B to C3b bound to a cellular membrane; Factor D; fragments Ba and Bb, which form upon cleavage of Factor B by Factor D; C3bBb or the alternative pathway C3-convertase; C3bBb3b, which cleaves C5 into C5a and C5b; C5 and fragments thereof (C5a and C5b); C6; C7; C8; C9; and the membrane attack complex (comprising C5b, C6, C7, C8, and C9). IgA is associated with activating the alternative path. In some embodiments of the methods and assays described herein, the immune protein is C3b, complex C3bB, or the membrane attack complex comprising C5b, C6, C7, C8, and C9.

The mannose-binding lectin pathway includes mannose binding lectin (MBL), which is a 2- to 6-headed molecule that forms a complex with MASP-I (Mannan-binding lectin-Associated Serine Protease) and MASP-II, two protease zymogens. MBL comprises carbohydrate-recognizing heads that bind to specifically arranged mannose residues on the phospholipid bilayer of a pathogen, such as mannose residues on carbohydrate or glycoprotein components of microorganisms including bacteria such as *Salmonella*, *Listeria*, and *Neisseria* strains, fungal pathogens, such as *Candida albicans* and *Cryptococcus neoformans*, as well as viruses, such as HIV-1 and Respiratory syncytial virus (RSV). The recognition of carbohydrates on pathogens by MBL activates MASP-I and MASP-II to cleave complement components C4 and C2 into C4a, C4b, C2a, and C2b. In some embodiments of the methods and assays described herein, the immune protein is mannose binding lectin (MBL).

Immunoglobulins

In some embodiments of the aspects described herein, an immunoglobulin can be the immune protein or component of an immune protein-enriched fraction detected or targeted using the methods and assays described herein. Essentially any immunoglobulin known by those of skill in the art can be used to prepare an immunoglobulin-enriched fraction (i.e., an immune protein-enriched fraction).

Immunoglobulins are a family of polypeptides that have an immunoglobulin fold characteristic of antibody molecules, which typically contains two β sheets and a conserved disulphide bond. Members of the immunoglobulin superfamily are involved in many aspects of cellular and non-cellular interactions in vivo, including widespread roles in the immune system (for example, antibodies, T-cell receptor molecules, etc.), involvement in cell adhesion (for example, the ICAM molecules), and intracellular signaling (for example, receptor molecules, such as the PDGF receptor).

In some embodiments, the immunoglobulin used as the immune protein in the methods and assays described herein is an antibody molecule. In some such embodiments, the immunoglobulin is IgA, IgD, IgE, IgG, or IgM. In some such embodiments, the immunoglobulin is IgG1, IgG2, IgG3, or IgG4. In some such embodiments, the immunoglobulin is IgA1 or IgA2.

The basic structure of all antibody immunoglobulins is based upon a unit consisting of two light polypeptide chains and two heavy polypeptide chains. Each light chain comprises two regions known as the variable light chain region and the constant light chain region. Similarly, the immunoglobulin heavy chain comprises two regions designated the variable heavy chain region and the constant heavy chain region.

The constant region for the heavy or light chain is encoded by genomic sequences referred to as heavy or light constant region gene (CM) segments. The use of a particular heavy chain gene segment defines the class of immunoglobulin. For example, in humans, the μ constant region gene segments define the IgM class of antibody, whereas the use of a γ1, γ2, γ3, or γ4 constant region gene segment defines the IgG class of antibodies, as well as the IgG subclasses IgG1 through IgG4. Similarly, the use of α1 or α2 constant region gene segment defines the IgA class of antibodies as well as the subclasses, IgA1 and IgA2. The δ and ε constant region gene segments define the IgD and IgE antibody classes, respectively.

The variable regions of the heavy and light immunoglobulin chains together contain the antigen binding domain of the antibody. The variable regions require diversity of the antibody to permit binding to a wide range of antigens. Antibody binding to an antigen in circulation can form an immune complex, which can be enriched for using the methods and assays described herein.

Other Immune Proteins

Other immune proteins that are elicited in response to and that can bind a microbe, such as a bacterium, virus, or fungus, and can be used to form an immune protein-enriched fraction, are also contemplated for use in the methods and assays described herein. Such immune proteins should be able to bind to a microbe, thus forming an immune complex as the term is described herein, and can include, but are not limited to: C-reactive protein (CRP) which is found in the blood and can bind to phosphocholine expressed on the surface of dead or dying cells and some types of bacteria; serum amyloid P (SAP); collectins, including surfactant protein A (SP-A), surfactant protein D (SP-D), collectin liver 1 (CL-L1), collectin placenta 1 (CL-P1), conglutinin, collectin of 43 kDa (CL-43) and collectin of 46 kDa (CL-46), which comprise a C-type lectin domain that is also called a carbohydrate recognition domain (CRD) and is used to selectively bind to specific complex carbohydrates of microbes; peptidoglycan recognition proteins (PGRs); the LRR, XA21D; defensins (e.g., Defensin, alpha 1, Neutrophil defensin 1, Defensin, alpha 1B, Defensin, alpha 3, Neutrophil defensin 3, Defensin, alpha 4, Defensin-5, Defensin-6, Beta-defensin 1, Beta-defensin 2, Beta-defensin 103, Beta-defensin 107, Beta-defensin 110, Beta-defensin 136); liposaccharide binding protein (LBP); NOD proteins which interact with microbes via C-terminal leucine rich regions (NOD1, which recognizes peptidoglycan containing the muramyl dipeptide NAG-NAM-gamma-D-glutamyl-meso diaminopimelic acid, part of the peptidoglycan monomer in common gram-negative bacteria and just a few gram-positive bacteria, and NOD-2, which recognizes peptidoglycan containing the muramyl dipeptide NAG-NAM-L-alanyl-isoglutamine found in practically all bacteria); NALPS (NALP1, NALP2, NALP3, NALP4, NALP5, NALP6, NALP7, NALP8, NALP9, NALP10, NALP11, NALP12, NALP13, and NALP14), IPAF, and NAIP5/Bircle.

In some embodiments of the aspects described herein, an immune protein that is elicited in response to, and that can bind a microbe, such as a bacterium, virus, or fungus, and form an immune complex, and can be used to form an immune protein-enriched fraction, belongs to the group of molecules termed "pattern recognition receptors" or PRRs.

Pattern recognition receptors or PRRs refer to a variety of receptor molecules that can bind specifically to conserved portions of microbial molecules shared by groups of related microbes that are essential for the survival of those organisms and are not found associated with non-microbial cells, such as mammalian cells. These unique microbial molecules are referred to herein as "pathogen-associated molecular patterns" (PAMPs) or "microbe-associated molecular patterns" (MAMPs). Examples of microbial-associated molecular patterns that can be recognized by PRRs include, but are not limited to, lipopolysaccharide (LPS) from the outer membrane of the gram-negative cell wall of bacteria; bacterial lipoproteins and lipopeptides; porins in the outer membrane of the gram-negative cell wall of bacteria; peptidoglycan found abundantly in the gram-positive cell wall of bacteria and to a lesser degree in the gram-negative cell wall of bacteria; lipoteichoic acids found in the gram-positive cell wall of bacteria; lipoarabinomannan found in acid-fast cell walls; mannose-rich glycans (short carbohydrate chains with the sugar mannose or fructose as the terminal sugar), that are common in microbial glycoproteins and glycolipids but rare in those of humans; flagellin found in bacterial flagella; bacterial and viral nucleic acid, as bacterial and viral genomes contain a high frequency of unmethylated cytosine-guanine dinucleotide or CpG sequences (a cytosine lacking a methyl or CH3 group and located adjacent to a guanine), while mammalian DNA has a low frequency of CpG sequences and most are methylated which can mask recognition by pattern-recognition receptors, and human DNA and RNA does not normally enter cellular endosomes where the pattern-recognition receptors for microbial DNA and RNA are located; N-formylmethionine, an amino acid common to bacterial proteins; double-stranded viral RNA unique to many viruses in some stage of their replication; single-stranded viral RNA from many viruses having an RNA genome; lipoteichoic acids, glycolipids, and zymosan from yeast cell walls; and phosphorylcholine and other lipids common to microbial membranes.

Examples of PRRs that can be used as immune proteins or to form immune protein-enriched fractions for use in the methods and assays described herein include, but are not limited to, mannose receptors that bind mannose-rich glycans, the short carbohydrate chains with the sugar mannose or fructose as the terminal sugar that are commonly found in microbial glycoproteins and glycolipids but are rare in those of humans; scavenger receptors that can bind to bacterial cell wall components such as LPS, peptidoglycan and teichoic acids, and include, for example, CD36, CD68, and SRB-1; opsonin receptors, such as acute phase proteins circulating in the plasma, such as mannose-binding lectin and C-reactive protein (CRP) that binds to phosphorylcholine in bacterial membranes and phosphatidylethenolamine in fungal membranes, surfactant proteins found in the alveoli of the lungs, such as SP-A and SP-D; N-formyl Met receptors, such as FPR and FPRL1; CD14, which promotes the ability of TLR-4 to respond to LPS; CARD (caspase activating and recruitment domain)-containing proteins, such as RIG-1 (retinoic acid-inducible gene-1) and MDA-5 (melanoma differentiation-associated gene-5), that are cytoplasmic sensors that recognize both viral double-stranded and single-stranded RNA molecules produced in viral-infected cells and trigger the synthesis of cytokines called interferons that block viral replication within infected host cells; and members of the Toll-like receptors or TLR family, which directly or indirectly bind different microbial molecules.

The different members of the TLR family have binding specificities for different MAMPs, such that TLR-2 recognizes peptidoglycan, bacterial lipoproteins, lipoteichoic acid (LTA), and porins; TLR-4 recognizes lipopolysaccharide (LPS) from gram-negative bacterial cell wall, fungal mannans, viral envelope proteins, parasitic phospholipids, and heat-shock proteins; TLR-5 recognizes bacterial flagellin; TLR-1/TLR-2 pairs bind uniquely bacterial lipopeptides and glycosylphosphatidylinositol (GPI)-anchored proteins in parasites; TLR-2/TL6 pairs that bind lipoteichoic acid (LTA) from gram-positive bacterial cell walls, bacterial lipopeptides, and peptidoglycan; TLR-3, which binds double-stranded viral RNA; TLR-7, which binds single-stranded viral RNA, such as in HIV, rich in guanine/uracil nucleotide pairs; TLR-8, which binds single-stranded viral RNA; and TLR-9, which binds unmethylated cytosine-guanine dinucleotide sequences (CpG DNA) found in bacterial and viral genomes.

Patients and Patient Samples

A biological sample from a patient can be obtained from any organ or tissue in the individual to be analyzed using the methods and assays described herein, provided that the biological sample comprises an immune protein, such as a complement protein, IgA, IgD, IgE, IgG, IgM, or a pathogen recognition receptor (PRR). Such samples can be further processed, in some embodiments, to enrich the sample for a desired immune protein, thereby producing an "immune protein-enriched sample," as the term is used herein. In other embodiments, a biological sample can be further isolated or purified prior to preparing an immune protein-enriched fraction. For example, plasma and serum can be isolated from a whole blood sample by, e.g., treating the whole blood sample with an anticoagulant such as heparin and centrifuging the sample until the cells sediment to permit plasma to be removed from the upper aqueous layer. Proteins and nucleic acids can be detected from a biological sample or a sample that has been treated as described above or as known to those of skill in the art.

Some non-limiting examples of biological samples for use in the methods and assays described herein include a blood sample, a urine sample, a semen sample, a lymphatic fluid sample, a cerebrospinal fluid sample, a plasma sample, a serum sample, a pus sample, an amniotic fluid sample, a bodily fluid sample, a stool sample, an intestinal lavage sample, a biopsy sample, a swab sample, a mouthwash sample, a tissue sample, skin secretion sample, or a combination of such samples. For the methods described herein, it is preferred that a biological sample is from whole blood, plasma, an intestinal lavage sample, cerebral spinal fluid, joint fluid, serum, and/or a respiratory sample, such as a respiratory secretion, e.g., sputum, or respiratory lavage fluid, such as brocheoalveolar lavage fluid. The term biological sample encompasses samples derived from an initial sample, such as, for example, after further processing of a biological for use in the methods and assays described herein. Such derived samples can, for example, include nucleic acids or proteins extracted from the sample or obtained by subjecting the sample to techniques such as amplification of nucleic acids or reverse transcription of mRNA, isolation and/or purification of certain nucleic acids, proteins, other cytoplasmic or nuclear components, etc.

The terms "patient", "subject" and "individual" are used interchangeably herein, and refer to an animal, particularly a human, to whom it is desirable to analyze for the presence of immune system-stimulating microbes in a biological sample obtained from the subject. In some embodiments, a subject is need of diagnosis of a disease or disorder, for example, diagnosis of inflammatory bowel disease, an infectious disease, or an autoimmune disorder, whereby a biological sample is analyzed using the methods and assays described herein.

Preparing Immune Protein-Enriched Fractions

Immune protein-enriched fractions for use in the methods described herein are typically prepared by immunoprecipitation, which refers to a technique of precipitating a protein antigen or complex of proteins (e.g., an immune protein such as IgG, a PRR, or complement bound to a microbe) out of solution using an antibody that specifically binds to that particular protein antigen. Methods for performing immunoprecipitation of immune proteins are well known in the art and/or are described in e.g., U.S. Pat. No. 4,618,589, which is herein incorporated by reference in its entirety. A general overview of the considerations of immunoprecipitation methods is provided herein, and one of skill in the art can easily adapt these considerations to optimize an immunoprecipitation protocol for a desired immune protein for use in detecting bound microbes, as demonstrated herein.

Immunoprecipitation is an affinity based molecular "pull-down" method that permits one of skill in the art to purify complexes using any affinity binding agent that is e.g., directly conjugated to a polymeric support having a specific affinity for one or more particular biomolecular targets. The basic procedure of immunoprecipitation involves three stages. The first stage involves preparation of the antigen solution or lysate. The second stage involves pre-clearing the antigen solution or lysate of nonspecific background binding, and the third stage involves forming and purifying the immune complexes. Once purified, any of a number of methods can be employed to analyze the antigens and material "pulled-down" using the immunoprecipitation procedure. The variety of procedures that can be used in affinity based molecular pull down and immunoprecipitation techniques specifically are described in detail in Harlow, E. and Lane, D. (eds.), "Antibodies: a Laboratory Manual", Chapter 7, Cold Spring Harbor Press, NY (1988), the entirety of which is herein incorporated by reference.

In the various aspects and embodiments of the methods described herein, immunoprecipitation can performed using any biological sample obtained from a patient that is to be used as a solution for performing an immunoprecipitation. It is contemplated herein that, in some embodiments, a lysate is prepared from a patient sample comprising cells or tissue by contacting the sample with a mild detergent. The mild detergent is effective in removing membranes, interfering with many weak intermolecular interactions and releasing most antigens from the cell, without disrupting the conformation or biochemical activity of the antigens of interest, such as the immune protein bound to a microbe. Interferences from nonspecific binding proteins are minimized by pretreating the antigen solution with an antibody that does not bind the antigen of interest, such as an immune protein as described herein, to remove the nonspecific binding proteins.

Immunoprecipitation of intact protein complexes for analysis and assaying of microbes using the methods described herein, such as immune complexes present in a patient sample, works by selecting an affinity binding agent, such as an antibody or fragment thereof that targets a known protein, e.g., an immune protein, such as a complement protein, IgA, IgD, IgE, IgG, IgM, or a pathogen recognition receptor (PRR), that is believed to be a member of the complex. By targeting this known member with the antibody or fragment thereof it becomes possible to pull the entire protein complex out of solution and thereby identify and/or detect unknown components of the immune complex, such as a microbe bound to the immune protein. Immuoprecipitation of immune complexes for use in the methods described herein can be achieved by the addition of affinity binding agents, such as, in some embodiments, antibodies or fragments thereof, specific for the immune protein being enriched for, to the lysate or patient sample. Antibodies have high affinity for their respective antigens, so antibody-antigen complexes form rapidly. In some embodiments of the methods described herein, affinity binding agents for immunoprecipitation of immune complexes can comprise proteins or molecules that have specificity for a class or group of immune proteins being targeted, such as, for example, all human IgG molecules, regardless of subclass, or have specificity for a group of immune proteins sharing a common domain, for example.

Accordingly, the immunoprecipitation steps described herein can be used to generate immune protein-enriched fractions for use in the assays and methods described herein. "Immune protein-enriched fractions" refers to samples that are partially purified (e.g., by immunoprecipitation) such that the level of a desired or targeted immune protein (e.g., immunoglobulins, complement, PRR, or other soluble/circulating components of the innate or adaptive immune response) is increased in the sample by at least 10% compared to the original patient sample from which it is derived. In some embodiments, the immune protein level is increased in the enriched fraction by at least 20%, at least 30%, at least 40%, at least 50%, at least 60%, at least 70%, at least 80%, at least 90%, at least 95%, at least 99%, at least 1-fold, at least 2-fold, at least 5-fold, at least 10-fold, at least 25-fold, at least 50-fold, at least 100-fold, at least 1000-fold, or more, compared to the patient sample from which it is derived. The immune protein-enriched fractions thus generated are then used in the assays and methods described herein to identify any microbes bound to the targeted immune protein(s).

Any affinity binding agent having affinity and specificity for a target immune protein(s) can be used in an immunoprecipitation method, as described herein. An "affinity binding agent" is an agent, such as a protein, e.g., antibody or fragment thereof, that has high affinity and specificity for a target immune protein, class of immune proteins, or family of immune proteins, that can be used in the preparation of immune protein-enriched fractions for use the assays and methods described herein. The selection of an affinity binding agent for preparation of an immune-enriched fraction involves considerations known to one of ordinary skill in the art, such as availability of an affinity binding agent having the desired specificity and affinity, the number and/or type of different immune proteins to be targeted by the affinity binding agent, relative costs of different affinity binding agents having equivalent specificities and/or affinities, and the like.

Accordingly, in some embodiments of the methods described herein, an immune-enriched fraction is prepared using an antibody or fragment thereof as the affinity binding agent. Antibodies suitable for preparing immune-enriched fractions and practicing the immunoprecipitation steps of the MiIP-Seq methods and assays described herein are preferably monoclonal and specific, and can include, but are not limited to, mouse, rat, rabbit, donkey, goat, human, or chimeric antibodies, and can comprise single chain antibodies, Fab fragments, F(ab') fragments, fragments produced by a Fab expression library, and/or binding fragments of any of the above. Advantages of antibodies and antigen binding fragments thereof for use in the methods described herein include their ability to be generated against any desired immune protein, class of immune proteins, or family of immune proteins, as is known to one of ordinary skill in the art.

The term "monoclonal antibody" refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen, such as an immune protein. Furthermore, in contrast to polyclonal antibody preparations that typically include different antibodies directed against different determinants (epitopes) on an antigen, e.g., multiple sites on an immune protein, such as an IgG molecule or PRR, each monoclonal antibody is directed against a single determinant on the antigen. The modifier "monoclonal" is not to be construed as requiring production of the antibody by any particular method. For example, the monoclonal antibodies to be used in accordance with the invention can be made by the hybridoma method first described by Kohler et al., Nature 256:495 (1975), or can be made by recombinant DNA methods (see, e.g., U.S. Pat. No. 4,816,567). "Monoclonal antibodies" can also be isolated from phage antibody libraries using the techniques described in Clackson et al., Nature 352:624-628 (1991) or Marks et al., J. Mol. Biol. 222:581-597 (1991), for example. Numerous commercial sources exist for obtaining monoclonal antibodies or fragments thereof specific for immune proteins for use in the immunoprecipitation steps described herein including, but not limited to, BD Biosciences, eBiosciences, RnD Systems, Invitrogen, BioLegend, AbCam, and the like.

In some embodiments, an antibody for use in the immunoprecipitation steps of the methods described herein can be a bi- or multi-specific antibody. Such antibodies are useful when, for example, specificity against two or more immune proteins present in an immune protein-enriched fragment is desired. In some such embodiments, bispecific antibodies having an IgG-like format can be used, in which one antigen-binding region (comprised of a VH and a VL domain) specifically binds one immune protein, and the other antigen-binding region (also comprised of a VH and a VL domain) specifically binds another immune protein. In some embodiments, each of the variable regions (2 VH regions and 2 VL regions) is replaced with a dAb or single variable domain. The dAb(s) or single variable domain(s) that are included in an IgG-like format can have the same specificity or different specificities. In some embodiments, the IgG-like format is tetravalent and can have two, three or four specificities. Antigen-binding fragments of IgG-like formats (e.g., Fab, F(ab')2, Fab', Fv, scFv) can be prepared as is known to one of skill in the art. In other embodiments, bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies can be made using any convenient cross-linking methods. Suitable cross-linking agents are well known in the art, and are disclosed in U.S. Pat. No. 4,676,980, along with a number of cross-linking techniques.

In some embodiments, an antibody for use in the immunoprecipitation steps of the methods described herein can comprise an "antibody fragment" or "antibody fragment thereof." The terms "antibody fragment" or "antibody fragment thereof" as used herein, refer to a protein fragment that comprises only a portion of an intact antibody, generally including an antigen binding site of the intact antibody and thus retaining the ability to bind antigen, such as an immune protein. Examples of antibody fragments encompassed for use in the methods described herein include: (i) the Fab fragment, having VL, CL, VH and CH1 domains; (ii) the Fab' fragment, which is a Fab fragment having one or more cysteine residues at the C-terminus of the CH1 domain; (iii) the Fd fragment having VH and CH1 domains; (iv) the Fd' fragment having VH and CH1 domains and one or more cysteine residues at the C-terminus of the CH1 domain; (v) the Fv fragment having the VL and VH domains of a single arm of an antibody; (vi) the dAb fragment (Ward et al., Nature 341, 544-546 (1989)) which consists of a VH domain; (vii) isolated CDR regions; (viii) F(ab')2 fragments, a bivalent fragment including two Fab' fragments linked by a disulphide bridge at the hinge region; (ix) single chain antibody molecules (e.g. single chain Fv; scFv) (Bird et al., Science 242:423-426 (1988); and Huston et al., PNAS (USA) 85:5879-5883 (1988)); (x) "diabodies" with two antigen binding sites, comprising a heavy chain variable domain (VH) connected to a light chain variable domain (VL) in the same polypeptide chain (see, e.g., EP 404,097; WO 93/11161; and Hollinger et al., Proc. Natl. Acad. Sci. USA, 90:6444-6448 (1993)); (xi) "linear antibodies" comprising a pair of tandem Fd segments (VH—CH1-VH—CH1) which, together with complementary light chain polypeptides, form a pair of antigen binding regions (Zapata et al. Protein Eng. 8(10):1057-1062 (1995); and U.S. Pat. No. 5,641,870).

In some embodiments of the methods described herein, an immune-enriched fraction is prepared using a protein molecule that is not an antibody or antigen-binding fragment as the affinity binding agent, such as, for example, Protein A, Protein G, Protein A/G, Protein L, etc.

Protein A is a 40-60 kDa MSCRAMM surface protein originally found in the cell wall of the bacterium *Staphylococcus aureus*. Protein A comprises five homologous Ig-binding domains that fold into a three-helix bundle, each of which is able to bind proteins from many different mammalian species, most notably IgGs. It binds the heavy chain within the Fc region of most immunoglobulins and also within the Fab region in the case of the human VH3 family of antibodies. Protein A binds with high affinity to human IgG1, IgG2, and IgG4, as well as mouse IgG2a and IgG2b. Protein A binds with moderate to high affinity to human IgM, IgA and IgE, as well as to mouse IgG3 and IgG1. It does not react with human IgG3 or IgD, nor will it react to mouse IgM, IgA or IgE. Accordingly, in some embodiments of the methods described herein, Protein A is used as the affinity binding agent when the immune protein to be targeted in the methods described herein is human IgG1, human IgG2, human IgG3, or a combination thereof. In some embodiments of the methods described herein, Protein A is used as the affinity binding agent when the immune protein to be targeted in the methods described herein is human IgA, human IgM, human IgE, or a combination thereof. In some embodiments of the methods described herein, Protein A is used as the affinity binding agent when the immune protein to be targeted in the methods described herein is human IgG1, human IgG2, human IgG3, human IgA, human IgM, human IgE, or any combination thereof.

Protein G is an immunoglobulin-binding protein expressed in group C and G Streptococcal bacteria much like Protein A, but has differing specificities. It is a 65-kDa (G148 protein G) and a 58 kDa (C40 protein G) cell surface protein. The native molecule also binds albumin, however, because serum albumin is a major contaminant of antibody sources, the albumin binding site has been removed from recombinant forms of Protein G. Protein G binds with high affinity to all human IgG subclasses, i.e., human IgG1, human IgG2, human IgG3, and human IgG4, but not to human IgG, IgM, IgA, IgD, and IgE. Accordingly, in some embodiments of the methods described herein, Protein G is used as the affinity binding agent when the immune protein to be targeted in the methods described herein is human IgG1, human IgG2, human IgG3, human IgG4, or any combination thereof.

Protein A/G is a recombinant fusion protein that combines the IgG binding domains of both Protein A and Protein G. Protein A/G comprises four Fc binding domains from Protein A and two from Protein G. The binding of Protein A/G is less dependent upon pH than Protein A, but otherwise has the additive properties of Protein A and G. Protein A/G binds to all subclasses of human IgG, i.e., human IgG1, human IgG2, human IgG3, and human IgG4, as well as IgA, IgE, IgM and (to a lesser extent) IgD. Accordingly, in some embodiments of the methods described herein, Protein A/G is used as the affinity binding agent when the immune protein to be targeted in the methods described herein is human IgG1, human IgG2, human IgG3, human IgG4, IgA, IgE, IgM, IgD, or any combination thereof.

Protein L was first isolated from the surface of bacterial species *Peptostreptococcus magnus* and was found to bind immunoglobulins through L chain interaction. Protein L does not contain any interchain disulfide loops, nor does it consist of disulfide-linked subunits Unlike Protein A and Protein G, which bind to the Fc region of immunoglobulins, Protein L binds antibodies through light chain kappa interactions. Since no part of the heavy chain is involved in the binding interaction, Protein L binds a wider range of antibody classes than Protein A or G. Protein L binds to representatives of all antibody classes, including IgG, IgM, IgA, IgE and IgD. Single chain variable fragments (scFv) and Fab fragments also bind to Protein L. Protein L binding is restricted to those antibodies that contain kappa light chains, and of such antibodies only certain subtypes of kappa light chains. For example, it binds human VκI, VκIII and VκIV subtypes but does not bind the VκII subtype. Accordingly, in some embodiments of the methods described herein, Protein L is used as the affinity binding agent when the immune protein to be targeted is any human Ig molecule (IgG, IgM, IgA, IgE and IgD) that comprises a human VκI, VκIII and VκIV subtype light chain.

In some embodiments of the methods described herein, affinity binding agents having specificity for the immune protein being targeted, such as, for example, protein G, protein A, antibodies or fragments thereof that are specific for a particular protein or class/family/group of proteins, are immobilized on a solid-phase substrate such as superparamagnetic microbeads or on microscopic agarose or agarose resin (non-magnetic) beads. The immune protein complexes can then be purified by adding the affinity bead suspension, such as the protein A or protein G bead suspension, or beads precoated with an antibody or fragment thereof specific for an immune protein, such as anti-IgG, anti-IgA, or an anti-complement component precoated beads, e.g., MACS paramagnetic beads (Miltenyi Biotec), to the solution containing the antibody-antigen complexes. For example, when the immune protein-enriched fraction comprises IgG or IgA as the immune protein being precipitated, and Protein A or Protein G is used as the affinity binding agent, purification occurs because protein A and protein G have a high affinity for the Fc portion of the antibody.

In other embodiments, affinity binding agents, such as protein G, protein A, antibodies or fragments thereof that are specific for a particular protein or class/family/group of proteins, are added directly to the sample comprising the immune protein(s), such as immunoglobulins, PRRs, complement proteins, to be enriched. In such embodiments, the affinity binding agents are not attached to a solid-phase support, and thus, for example, affinity binding agents are free to float around the sample comprising the immune protein to be enriched and bind their target(s). Subsequently, beads coated with a second affinity binding agent, such as protein A/G having specificity to the first affinity binding agent(s), are added to the mixture of affinity binding agents, such as antibodies or fragments thereof, and immune protein complexes. The affinity binding agents, e.g., antibodies or fragments thereof, that are now bound to their immune protein targets, can then be bound by the second affinity binding agent conjugated to the beads.

After the targeted immune complex is bound to the bead through, for example, the immune protein A/G-antibody interaction, the beads are collected by centrifugation and the unbound proteins are removed by washing the beads. The beads can be washed by rinsing with a solution such as lysis buffer and removing the lysate and wash buffer by aspiration. Complete removal of the wash buffer is important to lower the background and improve the effectiveness of the immunoassay.

Beads or other solid-phase support platforms suitable for practicing the immunoprecipitation step of the MiIP-Seq methods described herein can be of any form or material known to one of skill in the art. Highly porous agarose beads, also known as agarose resins or slurries, can be used and have a very high potential binding capacity, as virtually the entire sponge-like structure of the agarose particle (50 to 150 μm in size) is available for attachment of affinity binding agents, such as antibodies or fragments thereof.

Superparamagnetic beads can also be used in some embodiments of the MiIP-Seq assays and methods described herein. Such magnetic beads are solid and typically spherical, depending on the type of bead, and binding of an affinity binding agent, such as an antibody or fragment thereof, Protein A, Protein G, etc., is limited to the surface of each bead. Magnetic beads are significantly smaller than agarose beads (1 to 4 μm), and while these beads do not have the advantage of a porous center to increase binding capacity, the greater number of magnetic beads per volume collectively gives magnetic beads an effective surface area-to-volume ratio for optimum binding. Commercially available magnetic beads can be distinguished based by size uniformity into monodisperse and polydisperse beads. Monodisperse beads, also called microbeads, exhibit exact uniformity, and therefore all beads exhibit identical physical characteristics, including the binding capacity and the level of attraction to magnets. Polydisperse beads, while similar in size to monodisperse beads, show a wide range in size variability (1 to 4 μm) that can influence their binding capacity and magnetic capture. Although both types of beads are commercially available for immunoprecipitation steps for use in the methods and assays described herein, the higher quality monodisperse superparamagnetic beads are more suitable for automatic protocols because of their consistent size, shape and performance. Monodisperse and polydisperse superparamagnetic beads are offered by many companies, including, but not limited to, Invitrogen, Thermo Scientific, and Millipore.

After completion of the formation and purification of the immune complexes, the resulting immunoprecipitated proteins or immune protein complexes can be further analyzed immediately or stored for subsequent analyses. Frequently, in traditional immunoprecipitation methods, this next step is the separation of proteins by SDS-PAGE. However, in the MiIP-Seq methods described herein, the immunoprecipitated immune complexes are next analyzed at the nucleic acid level, by lysis of microbial components or cells of the immunoprecipitated immune complexes, extraction of nucleic acids from the lysed microbial components, and sequencing of the extracted nucleic acids.

Extracting Microbial Nucleic Acids

Methods for extracting nucleic acids from a sample, such as a lysed extract of microbial components from an immunoprecipitated immune complex described herein, are routine in the art and include methods such as phenol-chloroform precipitation, spin column-based nucleic acid purification, ethanol precipitation, and column purification. These methods are well known in the art and kits for purification of nucleic acids are readily available from commercial sources such as QIAGEN™, MoBiol™, and SIGMA-ALDRICH®.

Sequencing Extracted Nucleic Acids

The nucleic acids extracted from an immune protein-enriched fraction can be sequenced by any method known in the art, including e.g., shotgun cloning and next generation sequencing methods.

In some embodiments of the methods and assays described herein, sequencing of extracted nucleic acids is performed using the Sanger sequencing method or a variant thereof. This process involves preparation of the sample, often a PCR product amplification product or amplicon. In some embodiments of the methods and assays described herein, the nucleic acids extracted from the immune protein-enriched fraction do not undergo amplification prior to sequencing. The extracted nucleic acid sample or amplicon thereof is then subjected to a sequencing reaction (i.e. ABI's BigDye terminator cycle reaction) in which DNA polymerase incorporates 2',3'-dideoxy-dNTP terminators to produce early chain termination DNA fragments. The reaction mix is analyzed using electrophoresis analysis and the sequencing results are shown in chromatogram graphs. In automated sequencers, one round of ABI's 96-channel capillary electrophoresis (CE) analysis generates a total of 96×700, or 67 kilobase (kbp) reads. In CE sequencing, the sequencing samples are prepared for each sequence and subsequently loaded onto a 96 well plate. CE on microchips, allowing faster and easier results, has been reported, but the mode of operation is fundamentally similar to that of the automated CE sequencer.

In some embodiments of the methods and assays described herein, the sequencing method used on the extracted nucleic acids is pyrosequencing. Pyrosequencing has been described in various publications and patents including e.g., U.S. Pat. Nos. 6,210,891, 7,264,929 and 7,335,762. In pyrosequencing, templates are prepared by emulsion PCR with one to two million beads deposited into PTP wells. Smaller beads with sulphurylase and luciferase attached thereto surround the template beads and individual deoxynucleotide phosphates (dNTPs) are sequentially dispensed over the across the wells. When a dNTP which is complementary to the template is incorporated into the growing strand a pyrophosphate (ppi) is released and converted to ATP. The ATP oxidizes the luciferin to oxyluciferin and light is released. A detector detected the light released and correlates that event with the dNTP incorporated. This technique provides for reads of about 400 bases and can detect a homopolymer string of around six bases.

In some embodiments of the methods and assays described herein, sequencing by ligation is used to sequence the extracted nucleic acids. Sequencing by ligation has been described in various publications and patents including U.S. Pat. Nos. 5,912,148 and 6,130,073. In "sequencing by ligation" around one hundred million emulsion PCR template beads are deposited onto a glass slide and a universal primer is annealed to the templates. Probes containing two interrogation bases, each set of interrogation bases having a selected dye associated with it are added to the templates and those complementary to the target sequence are annealed. The 16 different dinucleotides within the probes are encoded in 4 different dyes. Following four color imaging the ligated dinucleotide probes are chemically cleaved to generate a phosphate group. The cycle of hybridization, ligation, imaging and cleaving is repeated a total of seven times so that the correct two base sequence can be identified. Next the universal primer is removed from the template and a second ligation round is performed with an n-1 primer which sets the interrogation base one base to the 5′ end. Seven more rounds of hybridization, ligation, imaging and cleaving are performed and 3 more rounds of removal and ligation produces a string of 35 data bits encoded in color space. These are aligned to a reference genome to decode the DNA sequence.

There are two techniques that employ reversible terminators to accomplish DNA sequencing for use with the methods and assays described herein. In the first, bridge amplification of DNA fragments is randomly distributed across eight channels of a glass slide, to which high density forward and reverse primers are covalently attached. The solid phase amplification produces about 80 million molecular clusters from individual single strand templates. A primer is annealed to the free ends of templates in each molecular cluster. The polymerase extends and then terminates DNA synthesis from a set of four reversible terminators each labeled with a different dye. Unincorporated reversible terminators are washed away and base identification is done with four color imaging. Blocking and dye groups are removed by chemical cleavage so that another cycle can be performed. In the second technique using reversible terminators, billions of unamplified ssDNA templates are prepared with poly(dA) tails that hybridize to poly(dT) primers covalently attached to a glass slide. For one pass sequencing this primer-template complex is sufficient, but for two pass sequencing the template strand is copied, the original template is removed and annealing a primer directed toward the surface. Unlike the first reversible terminator technique the reversible terminators are all labeled with the same dye and dispensed individually in a predetermined order. An incorporation event results in a fluorescent signal. U.S. Pat. No. 7,169,560 describes methods utilizing this reversible primer technology.

In some embodiments of the methods and assays described herein, sequencing by fluorescence resonance energy transfer (FRET) signal generated during the incorporation, by DNA polymerase labeled with a FRET molecule, of a cognate dNTP labeled with a FRET molecule at its terminal phosphate group, is used on the extracted nucleic acids. The labeled dNTP is incorporated when it has the correct complementarity to the template strand and the FRET due to the interaction of the two FRET molecules marks the base extension event, giving rise to the sequence read. This method has the advantages in recording DNA polymerization in real time and regular DNA without any modification is synthesized, and thus longer DNA reads can be recorded (see e.g., U.S. Pat. No. 7,329,492; U.S. Pat. No. 7,361,466; Eid, J. et al. (2009) *Science* 323(5910):133-8).

Toward these ends of increased speed and decreased cost, developments including sequencing DNA by hybridization, by synthesis (3′-extension), by ligation, by polony polymerization, by nanopore, by polymerase incorporation of dye-labeled dNTPs, and a few others have been developed. The rapid progress in DNA sequencing technologies (e.g. 454's high throughput pyrosequencing (454 Life Sciences) (Margulies et al. (2005) Nature 437, 376-380; Wheeler et al. (2008) Nature 452, 872-826; Ronaghi, et al. (1996) Anal Biochem 242, 84-89; Ronaghi et al. (1998) Science 281, 363-365), Illumina/Solexa sequencing by synthesis from single clones on a surface (lllumina) (Margulies et al. (2005) Nature 437, 376-380; Wheeler et al. (2008) Nature 452, 872-826), ABI's SOLiD technology ("Supported Oligonucleotide Ligation and Detection", Applied Biosystems)) (Cloonan et al. (2008) Nat Methods 5, 613-619), genomics assays, and bioinformatics technologies have dramatically opened up the opportunities for researchers to obtain in depth molecular pictures of complex biological systems. Various types of high throughput DNA sequencing have been developed and used to delineate nuclei acid sequences. Such methods are applied in sequencing machines including, for example, the 454 GenomeSequencer FLX instrument (Roche Applied Science), the Illumina (Solexa) Genome Analyzer, the Applied Biosystems ABI SOLiD system, the Helicos single-molecule sequencing device (HeliScope), and the Ion semiconductor sequencing by Ion Torrent Systems Inc. See also, for example, US patent application publications No. 20110111401 and No. 20110098193. It is understood that as the sequencing technology evolves, the analysis of nucleic acids extracted by the methods described herein can be performed using any new sequencing method as one skilled in the art sees appropriate.

Shotgun Cloning

In some embodiments of the methods and assays described herein, shotgun sequence of extracted nucleic acids is employed. In shotgun sequencing, DNA is broken up randomly into numerous small segments, which are sequenced using the chain termination method to obtain "reads." Multiple overlapping reads for the target DNA are obtained by performing several rounds of this fragmentation and sequencing. Computer programs then use the overlapping ends of different reads to assemble them into a continuous sequence.

Typically, large molecules of DNA, often more than 100,000 bases (100 kb) in length, are fragmented and reduced to libraries of numerous sub-clones of approximately 1-4 kb for propagation and sequence analysis. Most large-scale DNA sequencing strategies depend on a multistep process to randomly fragment the target molecule into these smaller pieces, which are then enzymatically joined (ligated) into a cloning vector in a reaction that inserts one or more DNA fragments into a single site in each vector molecule (Fitzgerald et al., Nucleic Acids Res. 14:3753 (1992)). This ligation mixture is introduced into specific strains of *Escherichia coli* (*E. coli*), with each bacterial cell propagating one vector along with any DNA fragments it carries. The vector DNA, which may or may not contain an insert, is purified from each cell line and used as a template in an enzymatic sequencing reaction (Sanger et al., Proc Natl Acad Sci USA 74:5463 (1977); Prober et al., Science 238:336 (1987); Tabor and Richarson, Proc Natl Acad Sci USA 92:6339 (1995), all of which are hereby incorporated by reference). The reaction product is analyzed by automated sequencing instruments to determine the linear sequence of the sub-cloned DNA fragments (Smith et al., Nature 321:674 (1986), hereby incorporated by reference). Computer algorithms are used to assemble the data from the library of sub-fragments, typically producing sequence information for 80-95% of the original DNA molecule. "Gap filling" techniques are used to determine the remaining 5-20% of the target DNA.

Next-Generation Sequencing

Another method contemplated herein for sequencing extracted nucleic acids in the methods and assays described herein is "next-generation sequencing." These technologies produce shorter reads (anywhere from 25-500 bp) but produce many hundreds of thousands or millions of reads in a relatively short time (e.g., in one day). These technologies are superior to shotgun sequencing due to the high volume of data and the relatively short time it takes to sequence a whole genome. The major disadvantage is that the accuracies are usually lower (although this is compensated for by the high coverage).

Next generation sequencing methods typically employ high-throughput technologies that parallelize the sequencing process, producing thousands or millions of sequences at once. High-throughput sequencing technologies are intended to lower the cost of DNA sequencing beyond what is possible with standard dye-terminator methods. Some non-limiting examples of next generation sequencing methods and machines include, but are not limited to, Massively Parallel Signature Sequencing (MPSS), 454 Pyrosequencing, the 454 GenomeSequencer FLX instrument (Roche Applied Science), Illumina (Solexa) sequencing, SOLiD sequencing, the Applied Biosystems ABI SOLiD system, the Helicos single-molecule sequencing device (HeliScope), and the Ion semiconductor sequencing by Ion Torrent Systems Inc. One of skill in the art can apply these sequencing methods, as well as any new sequencing methods to the assays and methods described herein.

Metagenomics

As known in the art, the term "metagenome" defines the totality of all genomes of organisms of a given habitat (e.g., a patient sample) (see e.g., Handelsman et. al. (1998) *Chemistry and Biology* 5:245-249). In particular, the term "metagenome" relates to genomic nucleic acids, preferably DNA, derived from microorganisms including cultivatable and uncultivatable microbes, i.e., organisms that cannot be isolated by standard methods and made actively replicating in standard artificial media for indefinite periods of time. Particularly the representation of any particular microbial genome in the extracted portion of the metagenome is not influenced by or dependent on the cultivatability of this organism. Therefore nucleic acids of both uncultivated and uncultivatable microbes are substantially represented in the extracted fraction of the metagenome.

Accordingly, in some embodiments of the methods and assays described herein, metagenomics involves direct extrusion of DNAs from patient samples and their propagation and expression into a cultivated host cell, typically a bacteria. Metagenomics was first developed and used for the identification of new bacterial phylum (Pace 1997) based on the specific cloning of genes recognized for their interest as phylogenetic markers, such as 16S rDNA genes.

More recent developments of metagenomics consider the total metagenome cloned without any selection and/or identification to establish random "Metagenomic DNA libraries". This provides access to the whole genetic potential of bacterial diversity without any particular selection. Metagenomic DNA libraries are composed of hundreds of thousands of clones which differ from each other by the environmental DNA fragments which have been cloned. In this respect, large DNA fragments have been cloned (more than 30 Kb), so as to (i) limit the number of clones which have to be analyzed and (ii) to be able to recover whole biosynthetic pathways for the identification of new metabolites resulting from multi enzymatic synthesis.

Comparing Sequences to Those of Known Microbes

In some embodiments of the methods and assays described herein, the sequences of the extracted nucleic acids, obtained using any of the above-described methods or those known to one of ordinary skill in the art, are compared to known sequences of microbes e.g., a database of microbial gene sequences such as GenBank, or GreenGenes (found on the worldwide web at greengenes.lbl.gov), as a library of 16S sequences and their annotation, and the sample sequences can be identified using search tools such as BLAST to query the database for nucleic acid sequence homology. In some such embodiments, the database comprises metagenomic data derived from a population of microbes.

If the compared sequences have less than 20% homology, it is determined that the extracted and sequenced nucleic acids are derived from a previously uncharacterized microbe, while if the compared sequences have greater than 20% homology, it is determined that the microbes with greater than 20% homology are from the same family of microbes.

Diseases and Disorders

The assays and methods described herein are useful, in some aspects and embodiments, for identifying and diagnosing the presence of an immune-stimulating microbe in a subject or patient having a disease or disorder.

Inflammatory Bowel Disease

In some embodiments, the methods and assays described herein are useful for the diagnosis of inflammatory bowel disease and/or identification of microbe(s) eliciting immune responses in a subject having inflammatory bowel disease.

Inflammatory bowel diseases (IBDs) are defined by chronic, relapsing intestinal inflammation of obscure origin. The etiology of IBD is still not well understood. There is however a growing consensus, based both on patient studies and from transgenic animal models of colitis, that the intestinal inflammation results from an abnormal response to non-pathogenic intestinal bacteria. Some of the most striking evidence for the involvement of bacteria in IBD pathogenesis comes from studies demonstrating the presence of *E. coli* in ileal mucosal biopsies taken from Crohn's disease patients. These organisms, despite lacking conventional markers of bacterial pathogenicity, are able to invade intestinal cell lines and to live within macrophages without inducing apoptosis. Other studies, which used a broad-specificity 16S ribosomal probe for in situ hybridization to detect bacteria of all species, found an increase in unidentified bacteria within the mucus layer in both UC and CD. Further, the genetic basis for IBD overlaps with that described for responses to infectious agents such as leprosy, raising the possibility, without wishing to be bound or limited by a theory, that IBD occurs as a response to an exogenous infectious agent (N Engl J Med 2010).

Inflammatory bowel diseases include e.g., Crohn's disease, ulcerative colitis, collagenous colitis, lymphocytic colitis, ischemic colitis, diversion colitis, Behcet's syndrome, or indeterminate colitis. However, the most common inflammatory bowel diseases are Crohn's disease and ulcerative colitis. These diseases appear to result from the unrestrained activation of an inflammatory response in the intestine. This inflammatory cascade is perpetuated, in part, through the actions of pro-inflammatory cytokines and selective activation of lymphocyte subsets. In patients with IBD, ulcers and inflammation of the inner lining of the intestines lead to symptoms of abdominal pain, diarrhea, and rectal bleeding. Ulcerative colitis occurs in the large intestine, while in Crohn's, the disease can involve the entire GI tract as well as the small and large intestines. For most patients, IBD is a chronic condition with symptoms lasting for months to years. It is most common in young adults, but can occur at any age. It is found worldwide, but is most common in industrialized countries such as the United States, England, and northern Europe. It is especially common in people of Jewish descent and has racial differences in incidence as well. The clinical symptoms of IBD are intermittent rectal bleeding, crampy abdominal pain, weight loss and diarrhea. Diagnosis of IBD is based on the clinical symptoms, the use of a barium enema, but direct visualization (sigmoidoscopy or colonoscopy) is the most accurate test. Protracted IBD is a risk factor for colon cancer, and treatment of IBD can involve medications and surgery.

Some patients with UC only have disease in the rectum (proctitis), while others can have disease limited to the rectum and the adjacent left colon (proctosigmoiditis). In some individuals, UC occurs in the entire colon (pancolitis). Symptoms of UC are generally more severe with more extensive disease (larger portion of the colon involved with disease). Similarly, the prognosis for patients with disease limited to the rectum proctitis or UC limited to the end of the left colon (proctosigmoiditis) is better then that of subjects having involvement of the entire colon in the disease.

In some cases, brief periodic treatments using oral medications or enemas may be sufficient to induce remission in patients with ulcerative colitis, that is, the lack of symptoms such as pain, bleeding, and weight loss. In those with more extensive disease, blood loss from the inflamed intestines can lead to anemia, and may require treatment with iron supplements or even blood transfusions. Rarely, the colon can acutely dilate to a large size when the inflammation becomes very severe. This condition is called toxic megacolon. Patients with toxic megacolon are extremely ill with fever, abdominal pain and distention, dehydration, and malnutrition. Unless the patient improves rapidly with medication, surgery is usually necessary to prevent colon rupture.

Crohn's disease can occur in all regions of the gastrointestinal tract. With this disease intestinal obstruction due to inflammation and fibrosis occurs in a large number of patients. Granulomas and fistula formation are frequent complications of Crohn's disease. In serious cases of Crohn's disease patients may require intravenous feeding, surgery and colostomy to treat the disease appropriately.

Patients having inflammatory bowel disease also have an increased risk of developing colon cancer. The risk for cancer begins to rise significantly after eight to ten years of IBD.

Once a positive diagnosis has been made, IBD can be treated pharmacologically, with anti-inflammatory drugs, such as salicylates. Salicylate preparations are effective in treating mild to moderate disease and also decrease the frequency of disease flares when the medications are taken on a prolonged basis. Examples of salicylates include sulfasalazine, olsalazine, and mesalamine. These medications are often given orally in high doses in order to achieve a maximal therapeutic benefit. In IBD patients that do not respond to salicylates or corticosteroids, medications that suppress the immune system are used. Examples of immunosuppressants include azathioprine and 6-mercaptopurine.

Autoimmune Disorders

The methods and assays described in the various aspects and embodiments herein can also be particularly beneficial for identifying novel microbe(s) associated with, eliciting, or underlying autoimmune disorders or autoimmune diseases. Broadly speaking "autoimmune disease" refers to a class of diseases in which a subject's own antibodies react with host tissue or in which immune effector T cells are autoreactive to endogenous self-peptides and cause destruction of tissue. Thus an immune response is mounted against a subject's own antigens, referred to as self-antigens. A "self-antigen" as used herein refers to an antigen of a normal host tissue. Normal host tissue does not include cancer cells. It is thought that, without wishing to be bound or limited by theory, that some autoimmune diseases may have an additional, to-date unidentified microbial etiological agent, trigger, or component, such as a bacteria, virus, or fungus, involved in the initiation or progression or etiology of the disease. Accordingly, the methods described herein can be used in a subject suffering from or predisposed to an autoimmune disease, whereby immune protein-enriched fractions are obtained from a sample from a subject, nucleic acids are extracted from the fraction, and the extracted nucleic acids are sequenced to identify any immune-stimulating microbes in the subject.

Accordingly, in some embodiments of the methods and assays described herein, the subject suffers from or is predisposed to an autoimmune disease including, but not limited to: rheumatoid arthritis, multiple sclerosis, systemic lupus erythematosus (SLE), autoimmune encephalomyelitis, myasthenia gravis (MG), Hashimoto's thyroiditis, Goodpasture's syndrome, pemphigus (e.g., pemphigus vulgaris), Grave's disease, autoimmune hemolytic anemia, autoimmune thrombocytopenic purpura, scleroderma with anti-collagen antibodies, mixed connective tissue disease, polymyositis, pernicious anemia, idiopathic Addison's disease, autoimmune-associated infertility, glomerulonephritis (e.g., crescentic glomerulonephritis, proliferative glomerulonephritis), bullous pemphigoid, Sjogren's syndrome, insulin resistance, and autoimmune diabetes mellitus (type 1 diabetes mellitus; insulin-dependent diabetes mellitus). Autoimmune disease has been recognized also to encompass atherosclerosis and Alzheimer's disease. In one embodiment of the aspects described herein, the autoimmune disease is selected from the group consisting of multiple sclerosis, type-I diabetes, Hashinoto's thyroiditis, rheumatoid arthritis, systemic lupus erythematosus, gastritis, autoimmune hepatitis, hemolytic anemia, autoimmune hemophilia, autoimmune lymphoproliferative syndrome (ALPS), autoimmune uveoretinitis, glomerulonephritis, Guillain-Barre syndrome, psoriasis and myasthenia gravis.

Systems

Also provided herein, in other aspects and embodiments are systems (and computer readable media for causing computer systems) to perform methods for detecting and/or identifying an immune system-stimulating microbe in a patient sample.

Embodiments of the systems provided herein can be described through functional modules, which are defined by computer executable instructions recorded on computer readable media and which cause a computer to perform method steps when executed. The modules described herein are segregated by function for the sake of clarity. However, it should be understood that the modules/systems need not correspond to discreet blocks of code and the described functions can be carried out by the execution of various code portions stored on various media and executed at various times. Furthermore, it should be appreciated that the modules can perform other functions, thus the modules are not limited to having any particular functions or set of functions.

The computer readable storage media #30 can be any available tangible media that can be accessed by a computer. Computer readable storage media includes volatile and nonvolatile, removable and non-removable tangible media implemented in any method or technology for storage of information such as computer readable instructions, data structures, program modules or other data. Computer readable storage media includes, but is not limited to, RAM (random access memory), ROM (read only memory), EPROM (erasable programmable read only memory), EEPROM (electrically erasable programmable read only memory), USB memory, flash memory or other memory technology, CD-ROM (compact disc read only memory), DVDs (digital versatile disks) or other optical storage media, magnetic cassettes, magnetic tape, magnetic disk storage or other magnetic storage media, cloud server memory systems, other types of volatile and non-volatile memory, and any other tangible medium which can be used to store the desired information and which can accessed by a computer including and any suitable combination of the foregoing.

Computer-readable data embodied on one or more computer-readable storage media can define instructions, for example, as part of one or more programs, that, as a result of being executed by a computer, instruct the computer to perform one or more of the functions described herein, and/or various embodiments, variations and combinations thereof. Such instructions can be written in any of a plurality of programming languages, for example, Java, J#, Visual Basic, C, C#, C++, Fortran, Pascal, Eiffel, Basic, COBOL assembly language, and the like, or any of a variety of combinations thereof. The computer-readable storage media on which such instructions are embodied can reside on one or more of the components of either of a system, or a computer readable storage medium described herein, or can be distributed across one or more of such components.

The computer-readable storage media can be transportable such that the instructions stored thereon can be loaded onto any computer resource to implement the aspects of the present invention discussed herein. In addition, it should be appreciated that the instructions stored on the computer-readable medium, described above, are not limited to instructions embodied as part of an application program running on a host computer. Rather, the instructions can be embodied as any type of computer code (e.g., software or microcode) that can be employed to program a computer to implement aspects of the present invention. The computer executable instructions can be written in a suitable computer language or combination of several languages. Basic computational biology methods are known to those of ordinary skill in the art and are described in, for example, Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001).

The functional modules of certain embodiments of the systems described herein include, at minimum, a determination system #40, a storage device #30, a comparison module #80, and a display module #110. The functional modules can be executed on one, or multiple, computers, or by using one, or multiple, computer networks. The determination system has computer executable instructions to provide e.g., sequence information in computer readable form.

The determination system #40, can comprise any system for sequencing an immune system-stimulating microbe. Such systems can include, but are not limited to, next-generation sequencing platforms, high throughput sequencing platforms, PCR or quantitative PCR machines or devices, etc., as known to one of ordinary skill in the art.

The information determined in the determination system can be read by the storage device #30. As used herein the "storage device" is intended to include any suitable computing or processing apparatus or other device configured or adapted for storing data or information. Examples of an electronic apparatus suitable for use with the present invention include a stand-alone computing apparatus, data telecommunications networks, including local area networks (LAN), wide area networks (WAN), Internet, Intranet, and Extranet, local and remote servers, and local and distributed computer processing systems. Storage devices also include, but are not limited to: magnetic storage media, such as floppy discs, hard disc storage media, remote or local servers, magnetic tape, optical storage media such as CD-ROM, DVD, electronic storage media such as RAM, ROM, EPROM, EEPROM and the like, general hard disks and hybrids of these categories such as magnetic/optical storage media. The storage device is adapted or configured for having recorded thereon nucleic acid sequence information. Such information can be provided in digital form that can be transmitted and read electronically, e.g., via the Internet, on diskette, via USB (universal serial bus) or via any other suitable mode of communication.

As used herein, "stored" refers to a process for encoding information on the storage device. Those skilled in the art can readily adopt any of the presently known methods for recording information on known media to generate manufactures comprising information relating to immune stimulating microbes.

In some embodiments, the reference data stored in the storage device to be read by the comparison module is e.g., sequence data obtained from an immune protein-enriched fraction obtained from a patient sample.

The "comparison module" #80 can use a variety of available software programs and formats for the comparison operative to compare sequence information data determined in the determination system to one or more reference samples and/or stored reference data. In some embodiments of the systems described herein, the comparison module is configured to use pattern recognition techniques to compare information from one or more entries to one or more reference data patterns. The comparison module can be configured using existing commercially-available or freely-available software for comparing patterns, and can be optimized for particular data comparisons that are conducted. The comparison module provides computer readable information related to the nucleic acid sequences of immune system-stimulating microbes.

The comparison module, or any other module of the invention, can include an operating system (e.g., UNIX) on which runs a relational database management system, a World Wide Web application, and a World Wide Web server. World Wide Web application includes the executable code necessary for generation of database language statements (e.g., Structured Query Language (SQL) statements). Generally, the executables will include embedded SQL statements. In addition, the World Wide Web application can include a configuration file which contains pointers and addresses to the various software entities that comprise the server as well as the various external and internal databases which must be accessed to service user requests. The Configuration file also directs requests for server resources to the appropriate hardware—as may be necessary should the server be distributed over two or more separate computers. In one embodiment, the World Wide Web server supports a TCP/IP protocol. Local networks such as this are sometimes referred to as "Intranets." An advantage of such Intranets is that they allow easy communication with public domain databases residing on the World Wide Web (e.g., the GenBank or Swiss Pro World Wide Web site). Thus, in some embodiments, users can directly access data (via Hypertext links for example) residing on Internet databases using a HTML interface provided by Web browsers and Web servers.

The comparison module provides a computer readable comparison result that can be processed in computer readable form by predefined criteria, or criteria defined by a user, to provide a content based in part on the comparison result that may be stored and output as requested by a user using a display module #110.

The content based on the comparison result, can be the identity of an immune system-stimulating microbe. Alternatively, the content based on the comparison result can be the lack of identify of an immune system-stimulating microbe, indicating that the microbe is a previously uncharacterized microbe.

In some embodiments of the systems described herein, the content based on the comparison result is displayed on a computer monitor #120. In some embodiments of the systems described herein, the content based on the comparison result is displayed through printable media #130, #140. The display module can be any suitable device configured to receive from a computer and display computer readable information to a user. Non-limiting examples include, for example, general-purpose computers such as those based on Intel PENTIUM-type processor, Motorola PowerPC, Sun UltraSPARC, Hewlett-Packard PA-RISC processors, any of a variety of processors available from Advanced Micro Devices (AMD) of Sunnyvale, Calif., tablet or mobile phone devices, or any other type of processor, visual display devices such as flat panel displays, cathode ray tubes and the like, as well as computer printers of various types.

In some embodiments of the systems described herein, a World Wide Web browser is used for providing a user interface for display of the content based on the comparison result. It should be understood that other modules of the invention can be adapted to have a web browser interface. Through the Web browser, a user may construct requests for retrieving data from the comparison module. Thus, the user will typically point and click to user interface elements such as buttons, pull down menus, scroll bars and the like conventionally employed in graphical user interfaces.

The methods described herein therefore provide for systems (and computer readable media for causing computer systems) to perform methods for detecting and/or identifying an immune system-stimulating microbe in a patient sample and optionally to diagnose the patient with an infectious disease.

Systems and computer readable media described herein are merely illustrative embodiments of the invention for performing methods of diagnosis in an individual, and are not intended to limit the scope of the invention. Variations of the systems and computer readable media described herein are possible and are intended to fall within the scope of the invention.

The modules of the machine, or those used in the computer readable medium, can assume numerous configurations. For example, function may be provided on a single machine or distributed over multiple machines.

Some aspects and embodiments disclosed herein can be illustrated by, for example any of the following numbered paragraphs 1. A method for identifying or diagnosing the presence of an immune-stimulating microbe in a patient having a disease or disorder, the method comprising:
   (a) extracting nucleic acids from an immune protein-enriched fraction obtained from a patient sample,
   (b) sequencing the extracted nucleic acids, and
   (c) comparing the sequence of the extracted nucleic acids to known microbial nucleic acid sequences to identify whether the nucleic acids extracted from the immune protein-enriched fraction are microbial, wherein if the extracted nucleic acids are microbial, the patient is diagnosed as having an immune-stimulating microbe.

2. A method for identifying or diagnosing the presence of an immune-stimulating microbe in a patient having a disease or disorder, the method comprising:
   (a) preparing an immune protein-enriched fraction from a patient sample,
   (b) extracting nucleic acids from the immune protein-enriched fraction,
   (c) sequencing the extracted nucleic acids, and
   (d) comparing the sequence of the extracted nucleic acids to known microbial nucleic acid sequences to identify whether the nucleic acids extracted from the immune protein-enriched fraction are microbial, wherein if the extracted nucleic acids are microbial, the patient is diagnosed as having an immune-stimulating microbe.

3. The method of any one of paragraphs 1 or 2, wherein the patient having a disease or disorder has an inflammatory bowel disease.

4. The method of paragraph 3, wherein the inflammatory bowel disease is Crohn's disease, ulcerative colitis, collagenous colitis, lymphocytic colitis, ischemic colitis, diversion colitis, Behcet's syndrome, or indeterminate colitis.

5. The method of any one of paragraphs 1-4, wherein the patient having a disease or disorder has an autoimmune disorder.

6. The method of any one of paragraphs 1-5, wherein the patient having a disease or disorder has cirrhosis, sepsis, or viremia.

7. The method of any one of paragraphs 1-6, wherein the immune protein-enriched fraction is prepared using an affinity binding agent specific for an immunoglobulin, a complement protein, or a pathogen recognition receptor.

8. The method of any one of paragraphs 1-7, wherein the immune protein-enriched fraction is prepared using an affinity binding agent specific for IgA, IgD, IgE, IgG, IgM, or any combination thereof.

9. The method of any one of paragraphs 1-8, wherein the immune protein-enriched fraction is prepared using an affinity binding agent specific for IgG.

10. The method of any one of paragraphs 1-9, wherein the immune protein-enriched fraction is prepared by immunoprecipitation using an affinity binding agent.

11. The method of any one of paragraphs 7-10, wherein the affinity binding agent is protein A, protein G, protein A/G, protein L, an immune protein-specific antibody or fragment thereof, or any combination thereof.

12. The method of any one of paragraphs 7-11, wherein the affinity binding agent or immune protein-specific antibody comprises an anti-human IgG, an anti-human IgA, an anti-human IgD, an anti-human IgE, an anti-human IgM, or any combination thereof agent or antibody.

13. The method of any one of paragraphs 7-12, wherein the affinity binding agent is specific for an immunoglobulin immune protein and binds to an epitope on the Fc fragment of the immunoglobulin immune protein.

14. The method of any one of paragraphs 7-13, wherein the affinity binding agent is not bound to a solid phase support.
15. The method of any one of paragraphs 7-13, wherein the affinity binding agent is bound to a solid phase support.
16. The method of paragraph 15, wherein the solid phase support comprises superparamagnetic microbeads, microscopic agarose beads, or agarose resin beads.
17. The method of any one of paragraphs 1-16, wherein the immune system-stimulating microbe being detected is a bacterium, fungus or a virus.
18. The method of any one of paragraphs 1-17, wherein the immune system-stimulating microbe being detected belongs to the taxon domain Archae, Bacteria, or Eukarya.
19. The method of any one of paragraphs 1-18, wherein the patient sample is a blood sample, a plasma sample, a urine sample, a cerebrospinal fluid sample, a mucous membrane sample, a fecal sample, an intestinal lavage sample, an intestinal fluid sample, a joint fluid sample, a respiratory sputum sample, or a bronchoalveolar lavage fluid sample.
20. The method of paragraph 19, wherein the intestinal lavage sample is an ileal lavage sample.
21. The method of any one of paragraphs 1-20, wherein the immune system-stimulating microbe being detected is a previously uncharacterized microbe.
22. The method of any one of paragraphs 1-21, wherein the sequencing step is performed using shotgun cloning, 16S rRNA/DNA amplification, and/or metagenomic sequencing.
23. The method of any one of paragraphs 1-22, wherein the sequencing of step (b) or step (c) is performed using microbe gene-specific primers.
24. The method of any one of paragraphs 1-22, wherein the sequencing of step (b) or step (c) is performed using primers that are not gene-specific.
25. The method of any one of paragraphs 1-24, wherein the patient sample from which the immune protein-enriched fraction is prepared does not undergo a cultivation step prior to the step of extracting nucleic acids.
26. An assay for direct detection of an immune system-stimulating microbe in a patient sample, the assay comprising the steps of:
    (a) extracting nucleic acids from the immune protein-enriched fraction prepared from a patient sample, and
    (b) sequencing the extracted nucleic acids present in the immune protein-enriched fraction to obtain a sequence of any immune system-stimulating microbes present in the patient sample.
27. An assay for direct detection of an immune system-stimulating microbe in a patient sample, the assay comprising the steps of:
    (a) preparing an immune protein-enriched fraction from a patient sample,
    (b) extracting nucleic acids from the immune protein-enriched fraction, and
    (c) sequencing the extracted nucleic acids present in the immune protein-enriched fraction to obtain a sequence of any immune system-stimulating microbes present in the patient sample.
28. The assay of any one of paragraph 26 or 27, wherein the immune protein-enriched fraction is prepared using an affinity binding agent specific for an immunoglobulin, a complement protein, or a pathogen recognition receptor.
29. The assay of any one of paragraphs 26-28, wherein the immune protein-enriched fraction is prepared using an affinity binding agent specific for IgA, IgD, IgE, IgG, IgM, or any combination thereof.
30. The assay of any one of paragraphs 26-29, wherein the immune protein-enriched fraction is prepared using an affinity binding agent specific for IgG.
31. The assay of any one paragraphs 26-30, wherein the immune protein-enriched fraction is prepared by immunoprecipitation using an affinity binding agent.
32. The assay of paragraph 31, wherein the affinity binding agent is protein A, protein G, protein A/G, protein L, an immune protein-specific antibody or fragment thereof, or any combination thereof.
33. The assay of any one of paragraphs 31 or 32, wherein the affinity binding agent or immune protein-specific antibody comprises anti-human IgG.
34. The assay of any one of paragraphs 28-33, wherein the affinity binding agent is specific for an immunoglobulin immune protein and binds to an epitope on the Fc fragment of the immunoglobulin immune protein.
35. The assay of any one of paragraphs 28-34, wherein the affinity binding agent is not bound to a solid phase support.
36. The assay of any one of paragraphs 28-34, wherein the affinity binding agent is bound to a solid phase support.
37. The assay of paragraph 36, wherein the solid phase support comprises superparamagnetic microbeads, microscopic agarose beads, or agarose resin beads.
38. The assay of any one of paragraphs 26-38, wherein the immune system-stimulating microbe being detected is a bacterium, fungus or a virus.
39. The assay of any one of paragraphs 26-39, wherein the immune system-stimulating microbe being detected belongs to the taxon domain Archae, Bacteria, or Eukarya.
40. The assay of any one of paragraphs 26-40, wherein the patient sample is a blood sample, a plasma sample, a urine sample, a cerebrospinal fluid sample, a mucous membrane sample, a fecal sample, an intestinal lavage sample, an intestinal fluid sample, a joint fluid sample, a respiratory sputum sample, or a bronchoalveolar lavage fluid sample.
41. The assay of paragraph 40, wherein the intestinal lavage sample is an ileal lavage sample.
42. The assay of any one of paragraphs 26-41, wherein the immune system-stimulating microbe being detected is a previously uncharacterized microbe.
43. The assay of any one of paragraphs 26-42, wherein the sequencing step is performed using shotgun cloning, 16S rRNA/DNA amplification, and/or metagenomic sequencing.
44. The assay of any one of paragraphs 26-43, wherein the sequencing of step (b) or step (c) is performed using microbe gene-specific primers.
45. The assay of any one of paragraphs 26-43, wherein the sequencing of step (b) or step (c) is performed using primers that are not gene-specific.
46. The assay of any one of paragraphs 26-45, wherein the patient sample from which the immune protein-enriched fraction is prepared does not undergo a cultivation step prior to the step of extracting nucleic acids.

47. The assay of any one of paragraphs 26-47, wherein the microbe cannot be cultivated using standard cultivation conditions.
48. A system for obtaining data from at least one test sample comprising nucleic acids extracted from an immune-protein enriched sample obtained from an at least one patient, the system comprising:
   a. a determination module configured to receive said at least one test sample comprising the extracted nucleic acids and perform at least one sequencing analysis on said at least one test sample to generate a sequencing data output;
   b. a storage device configured to store said sequencing data output from said determination module;
   c. a comparison module configured to receive said sequencing data output of the test sample comprising extracted nucleic acids and perform at least one sequencing analysis on said sequencing data output to determine the presence or absence of one of the following conditions and produce a comparison data output:
      i. the extracted nucleic acid sequence has 20% homology or greater to a sequence of a known family of microbes; or
      ii. the extracted nucleic acid sequence has less than 20% homology to a sequence of a known family of microbes;
   and
   d. a display module for displaying a content based in part on the comparison data output from said comparison module, wherein the content comprises a signal indicative that the extracted nucleic acid sequence has 20% homology or greater to a sequence of a known family of microbes; or signal indicative that the extracted nucleic acid sequence has less than 20% homology to a sequence of a known family of microbes.
49. The system of paragraph 46, wherein the content displayed on said display module further comprises a signal indicative of the patient being recommended to receive a particular treatment regimen.

EXAMPLES

Provided herein are assays and methods to directly identify microbes to which the innate or adaptive immune system is responding. The mammalian host (human and non-human) is colonized by a wide variety of either commensal or pathogenic microbes. The response of the immune system is a fingerprint for commensalism or pathogenicity. Current microbiologic methods do not necessarily take into account the immune response to an organism as a means to directly identify the organism. Immune responses are defined to indirectly show the evidence of a microbe based upon the presence of immune response. As a corollary, the presence of the microbe is typically determined by cultivation or similar types of biologic assays. The assays and methods described herein couple the immune response with direct detection of microbes for the purposes of diagnosis and identification of specific infectious diseases, especially those in which the organism cannot be cultivated. Moreover, this method is amenable to direct application of a broad range of direct analysis of bodily fluids.

In some embodiments, the assays and methods described herein comprise the direct immunoprecipitation of IgG molecules by a variety of different approaches (for example protein A or protein G sepharose, antibodies specific for the Fc fragment of IgG) directly from bodily fluids (e.g. intestinal fluids, blood, joint fluid, cerebrospinal fluid). Once precipitated, nucleic acids are directly extracted from the immunoprecipitates. The sequencing can be performed on the DNA with primers that are designed to detect particular microbes, or 16S rRNA/DNA amplification or shotgun cloning and metagenomic sequencing can be performed to search for microorganisms across the spectrum of prokaryotic and eukaryotic kingdoms. Thus, the assays and methods described herein combine the selectivity of an immune response with the sensitivity and specificity of DNA sequencing. This method can be adapted to the sequencing of ribonucleic acids by first converting these to complementary DNA or directing the precipitation to other components of the immune response (e.g. IgM, IgE, IgA, IgD or even components of the innate immune response such as a complement). The assays and methods described herein also have broad veterinary applications, as well as applications in identifying organisms whose genetic material is not DNA but rather RNA and amenable to reverse-transcription.

Figure 1B:
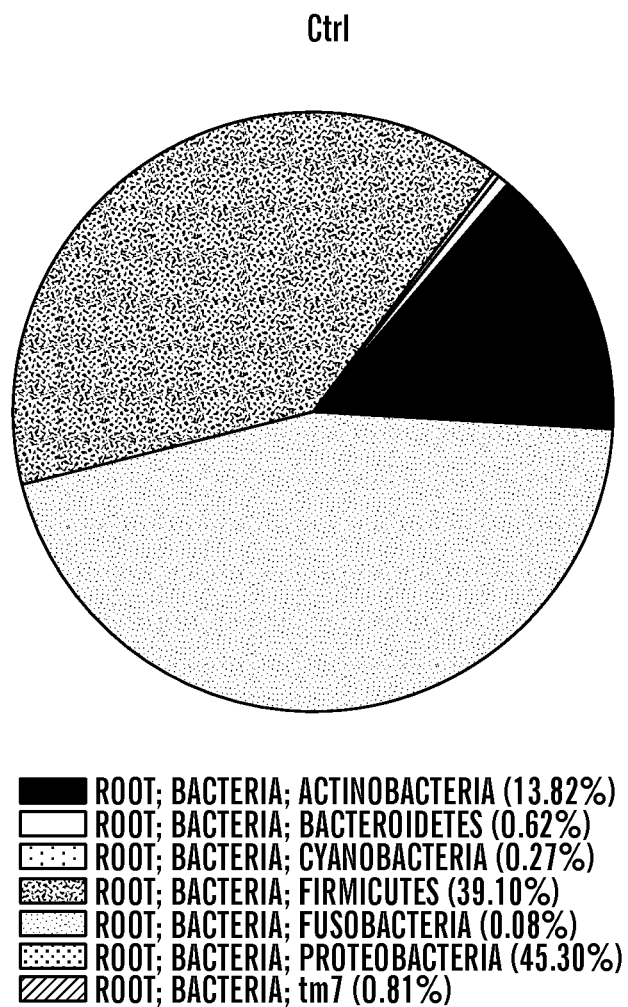
Figure 1C:
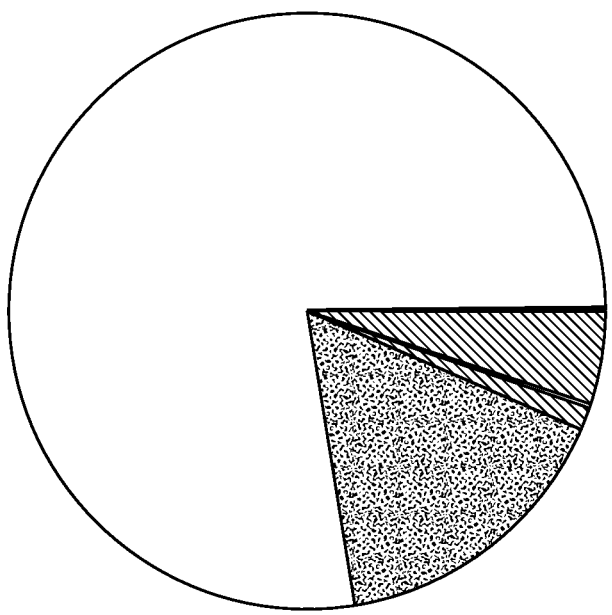
Figure 2A:
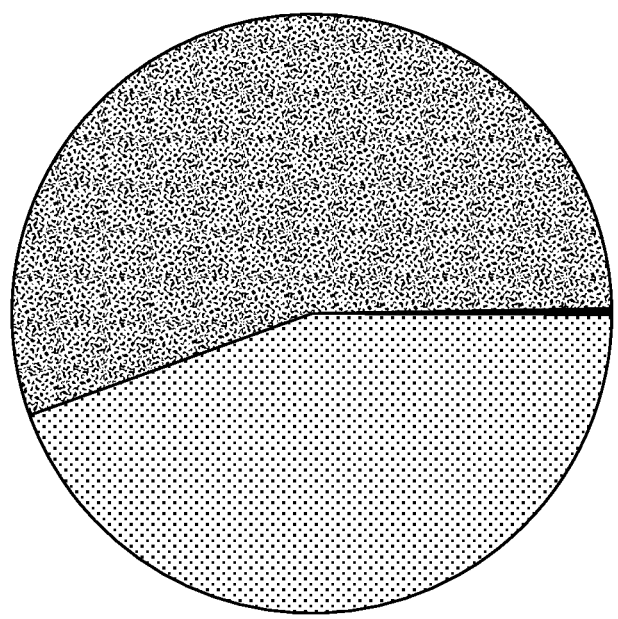
FIGS. 2A-2C depict a series of pie charts showing the proportion of bacteria in ileal lavage samples.
Figure 2B:
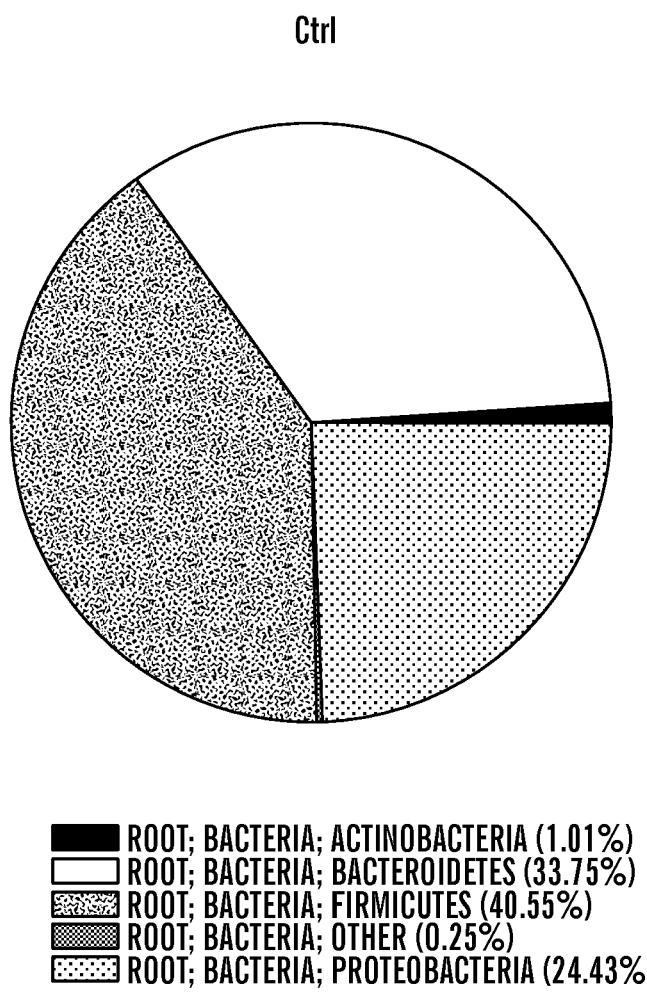
Figure 2C:
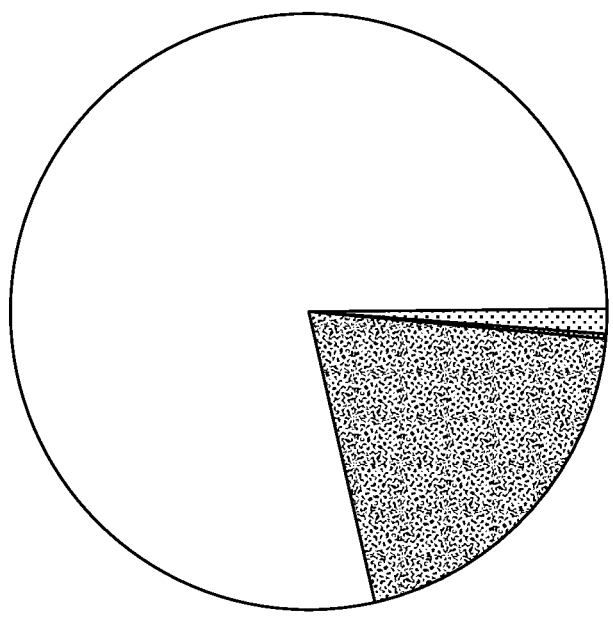

For example, FIGS. 1A-1C and 2A-2C demonstrate that microbial populations identified from ileal lavage samples differ depending upon the method by which they are isolated, as depicted using a series of pie charts showing the proportion of bacteria in ileal lavage samples. FIG. 1A shows an ileal lavage sample of a patient, while FIG. 1B shows the same ileal lavage sample immunoprecipitated using uncoated beads (i.e., control), and FIG. 1C shows an IgG-enriched fraction prepared by immunoprecipitation of the same ileal lavage sample using anti-human-IgG coated beads. A difference in abundance of 10 PCR cycles was observed between the IgG enriched fraction and the control uncoated beads fraction (i.e., greater than 1000-fold enrichment in the IgG beads over the control beads). DNA was isolated from anti-IgG beads and control beads after undergoing immunoprecipitation procedures from intestinal lavages as described herein, as well as from input-lavage; primers amplifying the V2 region of 16S DNA with appropriate adapters and linkers attached were used to generate a library that was then sequenced on a 454 sequencer. FIGS. 1A-1C show the relative abundance of sequences assigned to individual operational taxonomic units OTUs based on V2 homology and using public databases, such as greengenes.lbl.gov, found on the worldwide web, in anti-IgG immunoprecipitated lavage compared to control-precipitated lavage and input-lavage. To permit a qualitative comparison, the control uncoated bead immunoprecipitated DNA was amplified more extensively than the IgG beads DNA. The bacterial community in the lavage is very similar in composition to that precipitated with the control beads but is very different from the bacterial community pulled down by the IgG beads. Accordingly, the bacteria identified in the IgG-enriched fraction are "immune system-stimulating microbes," as that term is used herein. FIGS. 2A-2C demonstrate similar findings in regard to the bacterial communities identified in ileal lavage sample.

One of the advantages of the methods described herein, is that it is a non-cultivation method for identifying microbes that are being specifically responded to by one or more arms of the immune system, and thus have biologic relevance to a host, without the need for prior or subsequent cultivation steps. The assays can also be robotized into a high throughput format. The ability to sequence immune system-stimulating microbes using the methods and assays described herein allow direct detection of microbes for the purposes of diagnosis and identification of specific infectious diseases, especially those in which the organism cannot be cultivated.

Figure 3:
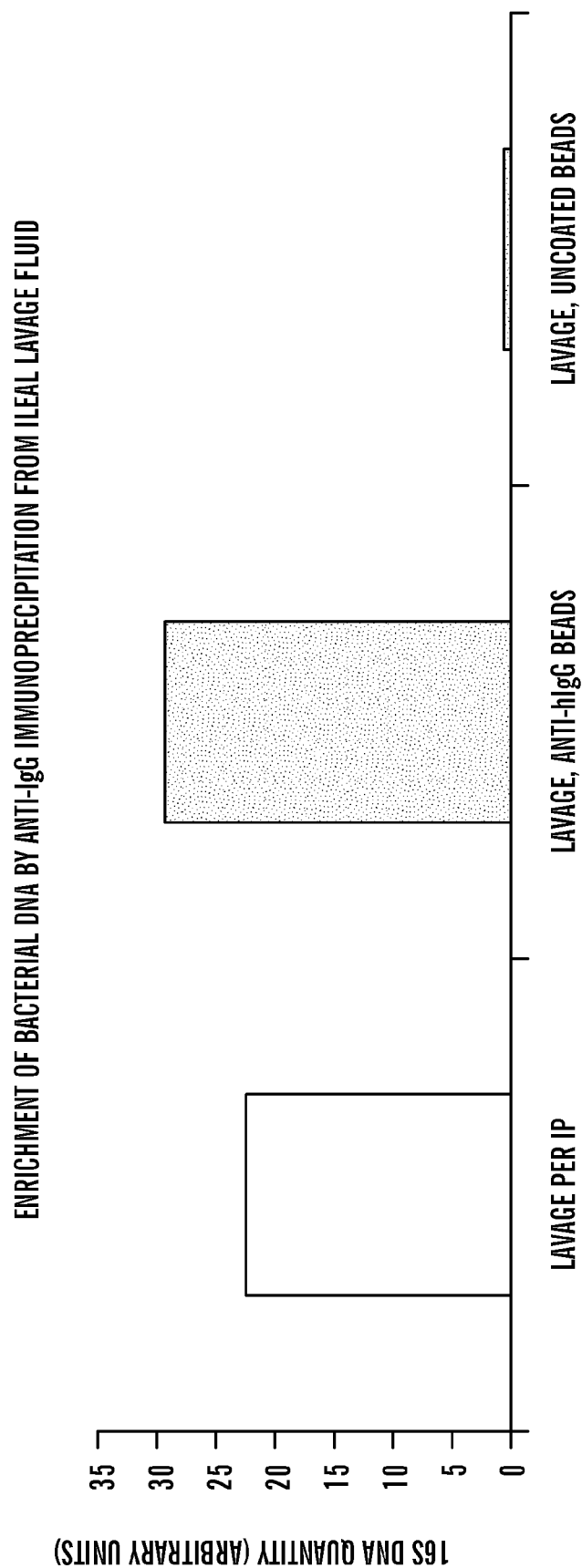
FIG. 3 is a graph showing that IgG-coated bacteria from small intestinal secretions from a patient with inflammatory bowel disease can be specifically pulled down and sequenced using 16S rDNA from immunoprecipitates, using an embodiment of the methods described herein. The abundance of 16S rDNA (representing the abundance of bacteria attached to the anti-IgG beads and control beads) was quantified by 16S rDNA specific primers via SYBR green-based quantitative real-time PCR. The bacteria in the IgG-enriched fraction is specific relative to a control (lavage, uncoated beads) and enriched by more than two logs or greater than 100-fold. These immunoprecipitates can comprise viable microbes, including bacteria that can be cultured. The immunoprecipitates can also comprise non-cultivatable microbes, which can require next-generation sequencing as well as shot-gun metagenomic, next-generation sequencing.

For example, as shown in FIG. 3, IgG-coated bacteria from small intestinal secretions from a patient with inflammatory bowel disease was specifically pulled down and sequenced using 16S rDNA from the immunoprecipitates, using an embodiment of the methods described herein. The abundance of 16S rDNA (representing the abundance of bacteria attached to the anti-IgG beads and control beads) was quantified by 16S rDNA specific primers via SYBR green-based quantitative real-time PCR. The bacteria in the IgG-enriched fraction is specific relative to a control (lavage, uncoated beads) and enriched by more than two logs or greater than 100-fold. The immunoprecipitates can also comprise non-cultivatable microbes, which can require next-generation sequencing as well as shot-gun metagenomic, next-generation sequencing.

Figure 4A:
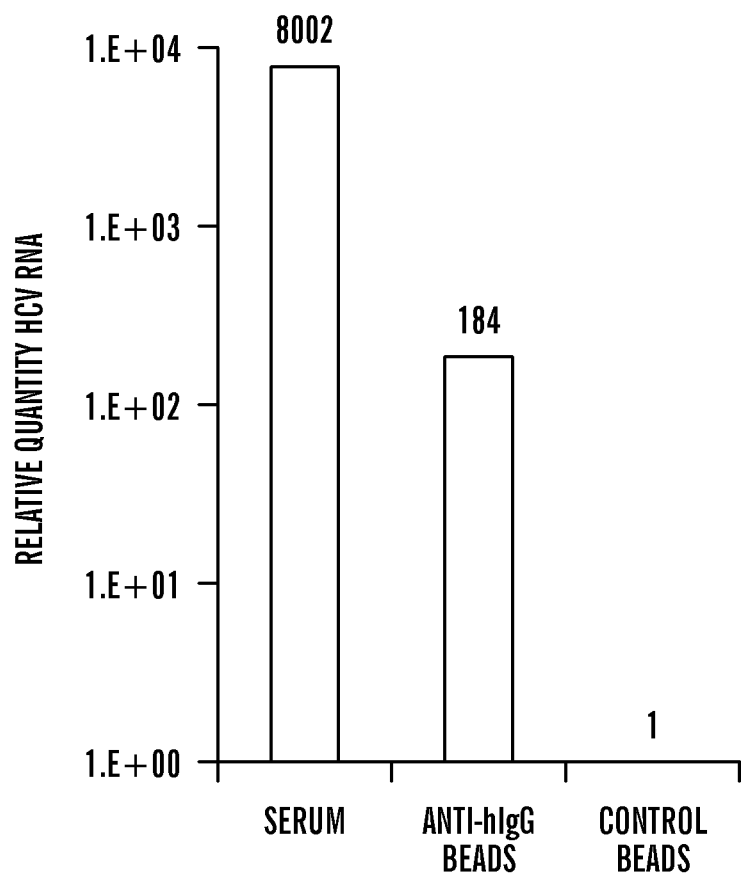
FIGS. 4A-4C demonstrate that embodiments of the immunoprecipitation methods described herein can be used to detect microbes, such as viruses, in samples deemed to be sterile using conventional methods. Serum from HCV-infected patients (individual patients in FIGS. 4A and 4C) was immunoprecipitated using either anti-IgG or control, as described herein, and RNA was isolated from anti-hIgG immunoprecipitates and control precipitates. RNA was reverse transcribed and tested for the presence of HCV cDNA using specific primers. A 184- and 117-fold enrichment of HCV signal was detected in anti-hIgG immunoprecipitates, and the virtual absence of signal in control precipitates is shown in FIG. 4C (same sample as FIG. 4A). These figures demonstrate that that the immunoprecipitation procedures described herein can be applied to otherwise "sterile" environments, like the peripheral blood, and demonstrates that these methods are capable of precipitating full viruses, as demonstrated herein using primers that specifically detect HCV RNA within this HCV-positive donor. The amplified products can then be detected via any sequencing-based approach, for example, metagenomic approaches in the context of viruses, or metagenomic or 16S-based approaches for bacteria, etc.
Figure 4B:
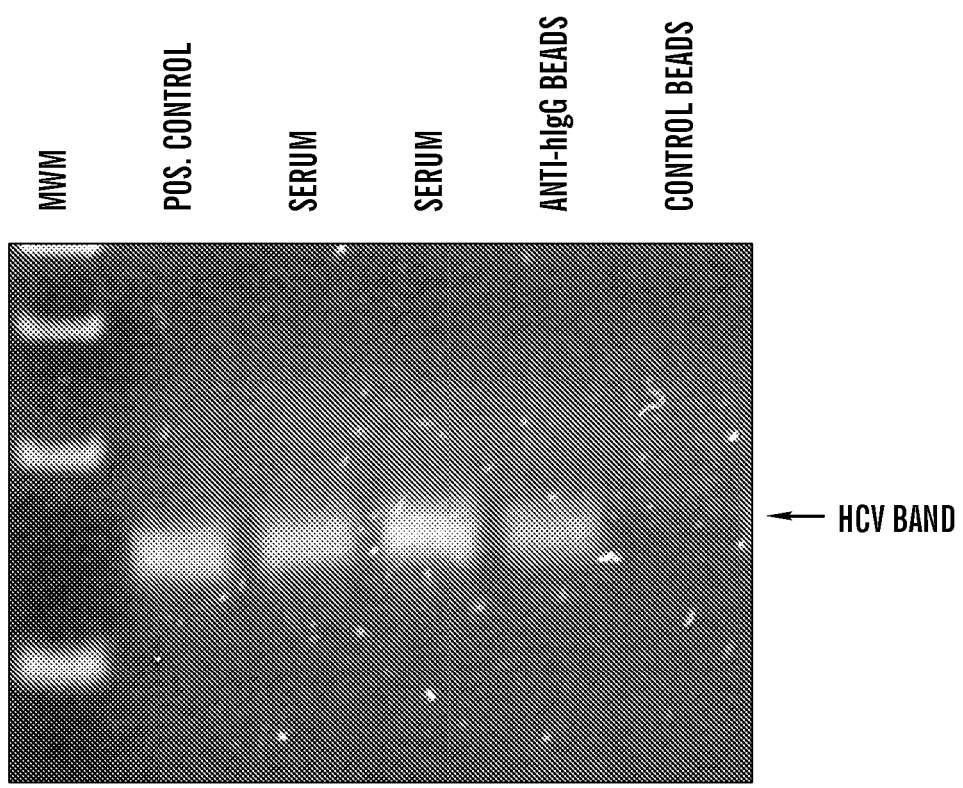
Figure 4C:
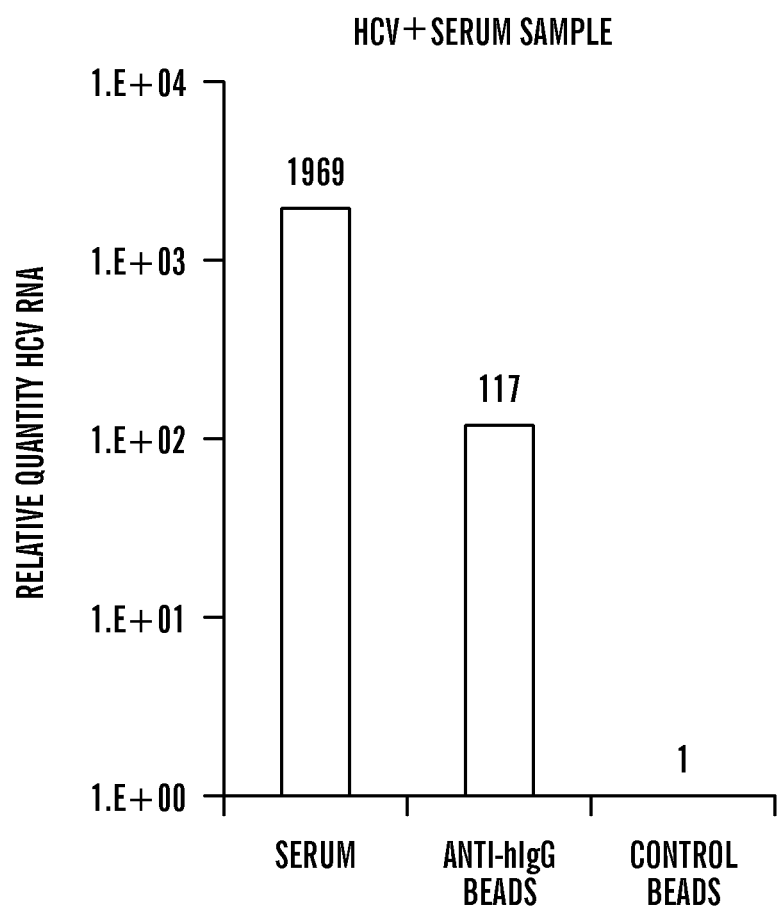
Figure 5:
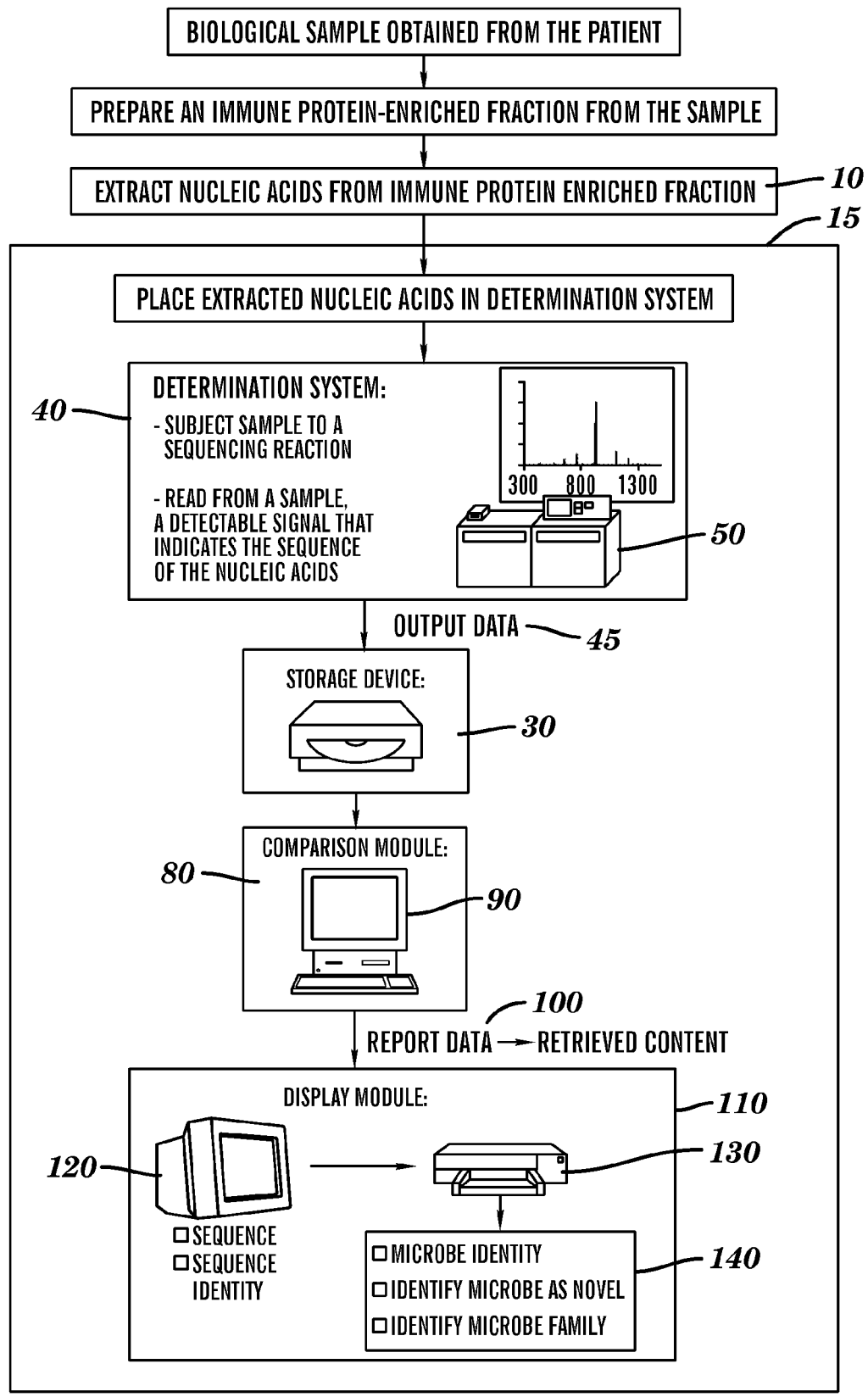
FIG. 5 is a block diagram depicting an exemplary system for use with the assays and methods described herein.
Figure 6:
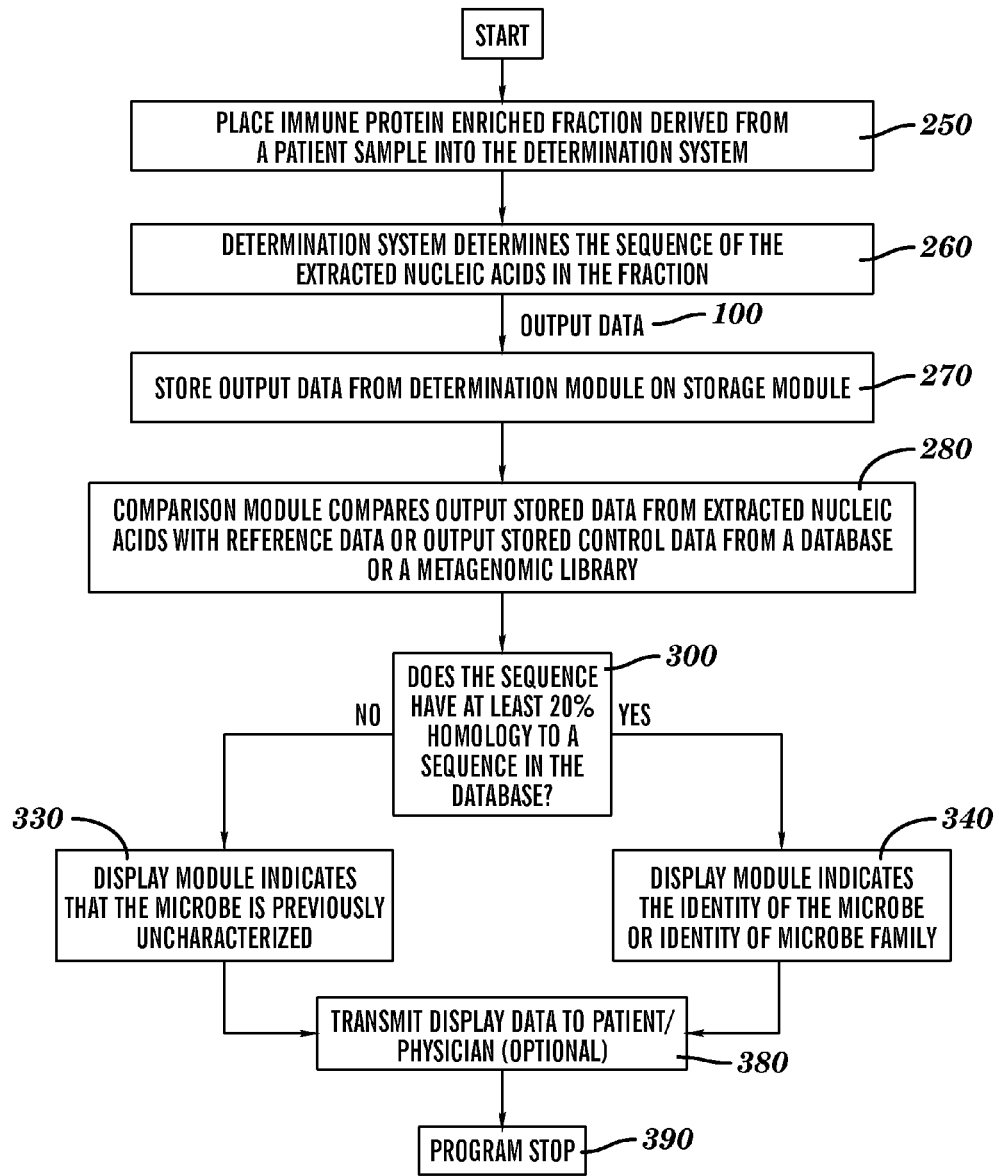
FIG. 6 is a block diagram depicting exemplary instructions encoded on a computer readable storage medium for use with the systems described herein.

The methods and assays described herein are also suitable for the identification of viruses in samples deemed to be sterile using conventional methods, as shown in FIGS. 4A-4C. Serum from HCV-infected patients (individual patients in FIGS. 4A and 4C) was immunoprecipitated using either anti-IgG or control, as described herein, and RNA was isolated from anti-hIgG immunoprecipitates and control precipitates. RNA was reverse transcribed and tested for the presence of HCV cDNA using specific primers. A 184- and 117-fold enrichment of HCV signal was detected in anti-hIgG immunoprecipitates, and the virtual absence of signal in control precipitates is shown in FIG. 4C (same sample as FIG. 4A). These figures demonstrate that that the immunoprecipitation procedures described herein can be applied to otherwise "sterile" environments, like the peripheral blood, and demonstrates that these methods are capable of precipitating full viruses, as demonstrated herein using primers that specifically detect HCV RNA within this HCV-positive donor. The amplified products can then be detected via any sequencing-based approach, for example, metagenomic approaches in the context of viruses, or metagenomic or 16S-based approaches for bacteria, etc.

These assays and methods are useful for the identification of novel pathogens for (emerging) infectious diseases as well as a diagnostic method for common (currently defined) infectious diseases. The methods described herein permit very rapid diagnosis as well as a real-time opportunity to detect biologic properties of an organism in vivo (e.g. antibiotic/antiviral resistance).

The invention claimed is:

1. A method for detecting the presence of an immune-stimulating microbe in a patient having an autoimmune disease or disorder, the method comprising:
   (a) extracting nucleic acids from an immune protein-enriched fraction obtained from a sample from a patient having an autoimmune disease or disorder,
   (b) amplifying the extracted nucleic acids using random primers to generate a library of amplified sequences and performing massively parallel sequencing on said library,
   (c) detecting whether an immune-stimulating microbe is present in the sample by comparing the sequences of the library of amplified sequences to known microbial nucleic acid sequences, wherein the presence of an immune stimulating microbe is detected when the comparing identifies microbial sequence in the amplified nucleic acids.

2. The method of claim 1, wherein the patient having an autoimmune disease or disorder has an inflammatory bowel disease.

3. The method of claim 1, wherein the immune protein-enriched fraction is prepared using an affinity binding agent specific for an immunoglobulin, a complement protein, or a pathogen recognition receptor.

4. The method of claim 1, wherein the immune protein-enriched fraction is prepared using an affinity binding agent specific for IgA, IgD, IgE, IgG, IgM, or any combination thereof.

5. The method of claim 1, wherein the immune system-stimulating microbe being detected is a bacterium, fungus or a virus.

6. The method of claim 1, wherein the patient sample is a blood sample, a plasma sample, a urine sample, a cerebrospinal fluid sample, a mucous membrane sample, a fecal sample, an intestinal lavage sample, an intestinal fluid sample, a joint fluid sample, a respiratory sputum sample, or a bronchoalveolar lavage fluid sample.

7. The method of claim 1, wherein the sequencing step is performed using shotgun cloning, 16S rRNA/DNA amplification, and/or metagenomic sequencing.

8. The method of claim 1, wherein the patient sample from which the immune protein-enriched fraction is prepared does not undergo a cultivation step prior to the step of extracting nucleic acids.

9. An assay for direct detection of an immune system-stimulating microbe in a patient sample, the assay comprising the steps of:
   (a) extracting nucleic acids from the immune protein-enriched fraction prepared from a sample from a patient having an autoimmune disease or disorder, and
   (b) amplifying the extracted nucleic acids present in the immune protein-enriched fraction using random primers to generate a library of amplified sequences and performing massively parallel sequencing on said library.

10. The assay of claim 9, wherein the immune protein-enriched fraction is prepared using an affinity binding agent specific for an immunoglobulin, a complement protein, or a pathogen recognition receptor.

11. The assay of claim 9, wherein the immune protein-enriched fraction is prepared using an affinity binding agent specific for IgA, IgD, IgE, IgG, IgM, or any combination thereof.

12. The assay of claim 11, wherein the affinity binding agent is not bound to a solid phase support.

13. The assay of claim 9, wherein the immune system-stimulating microbe being detected is a bacterium, fungus or a virus.

14. The assay of claim 9, wherein the patient sample is a blood sample, a plasma sample, a urine sample, a cerebrospinal fluid sample, a mucous membrane sample, a fecal sample, an intestinal lavage sample, an intestinal fluid sample, a joint fluid sample, a respiratory sputum sample, or a bronchoalveolar lavage fluid sample.

15. The assay of claim 9, wherein the sequencing step is performed using shotgun cloning, 16S rRNA/DNA amplification, and/or metagenomic sequencing.

16. The assay of claim 9, wherein the patient sample from which the immune protein-enriched fraction is prepared does not undergo a cultivation step prior to the step of extracting nucleic acids.

17. The assay of claim 9, wherein the microbe cannot be cultivated using standard cultivation conditions.

18. The method of claim 1, further comprising a step of preparing the immune protein-enriched fraction from the patient sample of step (a).

19. The assay of claim 9, further comprising a step of preparing the immune protein-enriched fraction from the patient sample of step (a).

\* \* \* \* \*